United States Patent
Kiniwa et al.

(10) Patent No.: US 11,089,271 B2
(45) Date of Patent: *Aug. 10, 2021

(54) 3 MOS CAMERA

(71) Applicant: PANASONIC I-PRO SENSING SOLUTIONS CO., LTD., Fukuoka (JP)

(72) Inventors: Yuji Kiniwa, Fukuoka (JP); Yota Hashimoto, Fukuoka (JP); Yuuichi Takenaga, Fukuoka (JP)

(73) Assignee: PANASONIC I-PRO SENSING SOLUTIONS CO., LTD., Fukuoka (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/085,192

(22) Filed: Oct. 30, 2020

(65) Prior Publication Data

US 2021/0127977 A1     May 6, 2021

(30) Foreign Application Priority Data

Oct. 31, 2019  (JP) .............................. JP2019-199182

(51) Int. Cl.
*H04N 9/04*      (2006.01)
*H04N 9/097*     (2006.01)
(Continued)

(52) U.S. Cl.
CPC ....... *H04N 9/04553* (2018.08); *H04N 5/2353* (2013.01); *H04N 5/33* (2013.01);
(Continued)

(58) Field of Classification Search
CPC . H04N 9/04553; H04N 9/04555; H04N 9/097
See application file for complete search history.

(56) References Cited

U.S. PATENT DOCUMENTS 5,777,674 A * 7/1998 Ohmuro ............. G02B 27/1013
                                                   348/265
2005/0057687 A1   3/2005 Irani et al.
(Continued)

FOREIGN PATENT DOCUMENTS

JP     2001-298749     10/2001
JP     2008-275582     11/2008
(Continued)

OTHER PUBLICATIONS

Notice of Reasons for Refusal from Japan Patent Office (JPO) in Japanese Patent Appl. No. 2019-199182, dated Jun. 16, 2020, together with an English language translation.
(Continued)

*Primary Examiner* — David N Werner
(74) *Attorney, Agent, or Firm* — Greenblum & Bernstein, P.L.C.

(57) ABSTRACT

A 3 MOS camera includes a first prism that has a first reflection film which reflects IR light that causes a first image sensor to receive the IR light, a second prism that has a second reflection film which reflects A % (A: a predetermined real number) visible light and that causes a second image sensor to receive the A % visible light, a third prism that causes a third image sensor to receive a (100–A) % visible light, and a video signal processor that combines a first video signal, a second video signal, and a third video signal of an observation part. The video signal processor performs pixel shifting on one of the second video signal and the third video signal having substantially same brightness to generate a fourth video signal and outputs a video signal obtained by combining the fourth video signal and the first video signal.

8 Claims, 18 Drawing Sheets

(51) Int. Cl.
*H04N 5/235* (2006.01)
*H04N 5/33* (2006.01)
*A61B 5/00* (2006.01)

(52) U.S. Cl.
CPC ............ *H04N 5/332* (2013.01); *H04N 9/097* (2013.01); *A61B 5/0071* (2013.01); *A61B 5/0077* (2013.01)

(56) References Cited

U.S. PATENT DOCUMENTS

| | | | | |
|---|---|---|---|---|
| 2008/0239501 | A1* | 10/2008 | Saita | G02B 27/142 |
| | | | | 359/634 |
| 2008/0246950 | A1 | 10/2008 | Ono | |
| 2009/0079834 | A1* | 3/2009 | Otsu | H04N 5/332 |
| | | | | 348/169 |
| 2009/0244717 | A1 | 10/2009 | Tocci | |
| 2010/0328780 | A1 | 12/2010 | Tocci | |
| 2011/0080487 | A1* | 4/2011 | Venkataraman | H04N 5/23296 |
| | | | | 348/218.1 |
| 2013/0194675 | A1 | 8/2013 | Tocci | |
| 2014/0320707 | A1* | 10/2014 | Olson | H04N 9/04553 |
| | | | | 348/262 |
| 2017/0219834 | A1* | 8/2017 | Horiguchi | H04N 5/335 |
| 2018/0249096 | A1* | 8/2018 | Toda | G02B 5/208 |
| 2018/0255252 | A1 | 9/2018 | Lewkow et al. | |
| 2018/0262725 | A1* | 9/2018 | Fan | H04N 9/097 |
| 2019/0361252 | A1* | 11/2019 | Nagae | G02B 21/0012 |
| 2020/0081235 | A1 | 3/2020 | Takahashi et al. | |

FOREIGN PATENT DOCUMENTS

| | | |
|---|---|---|
| JP | 2010-283564 | 12/2010 |
| JP | 2011-517192 | 5/2011 |
| JP | 2016-075825 | 5/2016 |
| JP | 2017-009396 | 1/2017 |
| JP | 2017-205492 | 11/2017 |
| JP | 2018-175762 | 11/2018 |
| WO | 2017/139596 | 8/2017 |
| WO | 2018/221041 | 12/2018 |

OTHER PUBLICATIONS

Decision to Grant a Patent from Japan Patent Office (JPO) in Japanese Patent Appl. No. 2019-199182, dated Sep. 8, 2020, together with an English language translation.

Extended Search Report from European Patent Office (EPO) in European Patent Appl. No. 20204311.3, dated Feb. 17, 2021.

* cited by examiner

3 MOS CAMERA

BACKGROUND OF THE INVENTION

1. Field of the Invention

The present disclosure relates to a 3 mos camera.

2. Background Art

In recent years, attention has been paid to a diagnosis method in which, at the time of surgery or examination, ICG (indocyanine green) is administered as a fluorescent reagent into a subject, and the ICG is excited by emission of excitation light or the like to capture and observe a near-infrared fluorescence image emitted by the ICG together with a subject image. For example, JP-A-2016-75825 discloses an imaging device having a blue separation prism that reflects a part of blue component light of incident light and near-infrared light in a specific wavelength region and transmits light other than the above light, a red separation prism that reflects a part of red component light of incident light and near-infrared light in a specific wavelength region and transmits light other than the above light, and a green separation prism into which the light transmitted through the red separation prism is incident.

SUMMARY OF THE INVENTION

In a configuration in JP-A-2016-75825, a partial light amount of the near-infrared light of light from a diseased part or the like is incident on each of the plurality of color separation prisms in a shared manner and imaged. For this reason, for example, there is a problem in that light specialized in the wavelength region of the near-infrared light cannot be received by a corresponding imaging element. Therefore, it is difficult to output a clearer fluorescence image of an observation part to which the fluorescent reagent is administered at the time of surgery or examination described above, and there is room for improvement in that a doctor or the like can more easily grasp the diseased part.

The present disclosure has been devised in view of the above-mentioned conventional circumstances, and a purpose is to provide a 3 mos camera that generates and outputs a clearer fluorescence image of an observation part to which a fluorescent reagent is administered to assist a doctor or the like in easily grasping a diseased part.

The present disclosure provides a 3 MOS camera used during a medical procedure including a first prism that has a first reflection film which reflects IR light of light from an observation part and that causes a first image sensor to receive the IR light, a second prism that has a second reflection film which reflects A % (A: a predetermined real number) of visible light transmitted through the first reflection film and which transmits remaining (100−A) % of the visible light and that causes a second image sensor to receive the A % visible light, a third prism that causes a third image sensor to receive the (100−A) % visible light transmitted through the second reflection film, and a video signal processor that generates a first video signal, a second video signal, and a third video signal of the observation part based on respective imaging outputs of the first image sensor, the second image sensor, and the third image sensor, combines the first video signal, the second video signal, and the third video signal, and outputs the combined video signal to a monitor. The video signal processor performs pixel shifting on one of the second video signal and the third video signal both having substantially same brightness as each other to generate a fourth video signal and outputs a video signal obtained by combining the fourth video signal and the first video signal to the monitor.

According to the present disclosure, it is possible to generate and output a clearer fluorescence image of an observation part to which a fluorescent reagent is administered, and it is possible to assist a doctor or the like in easily grasping a diseased part.

DETAILED DESCRIPTION OF THE EXEMPLARY EMBODIMENT

Hereinafter, embodiments that specifically disclose a 3 mos camera according to the present disclosure will be described in detail with reference to drawings as appropriate. However, more detailed description than necessary may be omitted. For example, detailed description of a well-known matter and redundant description of substantially the same configuration may be omitted. This is to prevent the following description from being unnecessarily redundant and to facilitate understanding by those skilled in the art. The accompanying drawings and the following description are provided for those skilled in the art to fully understand the present disclosure, and are not intended to limit subject matters described in claims thereby.

First Embodiment

Figure 1:
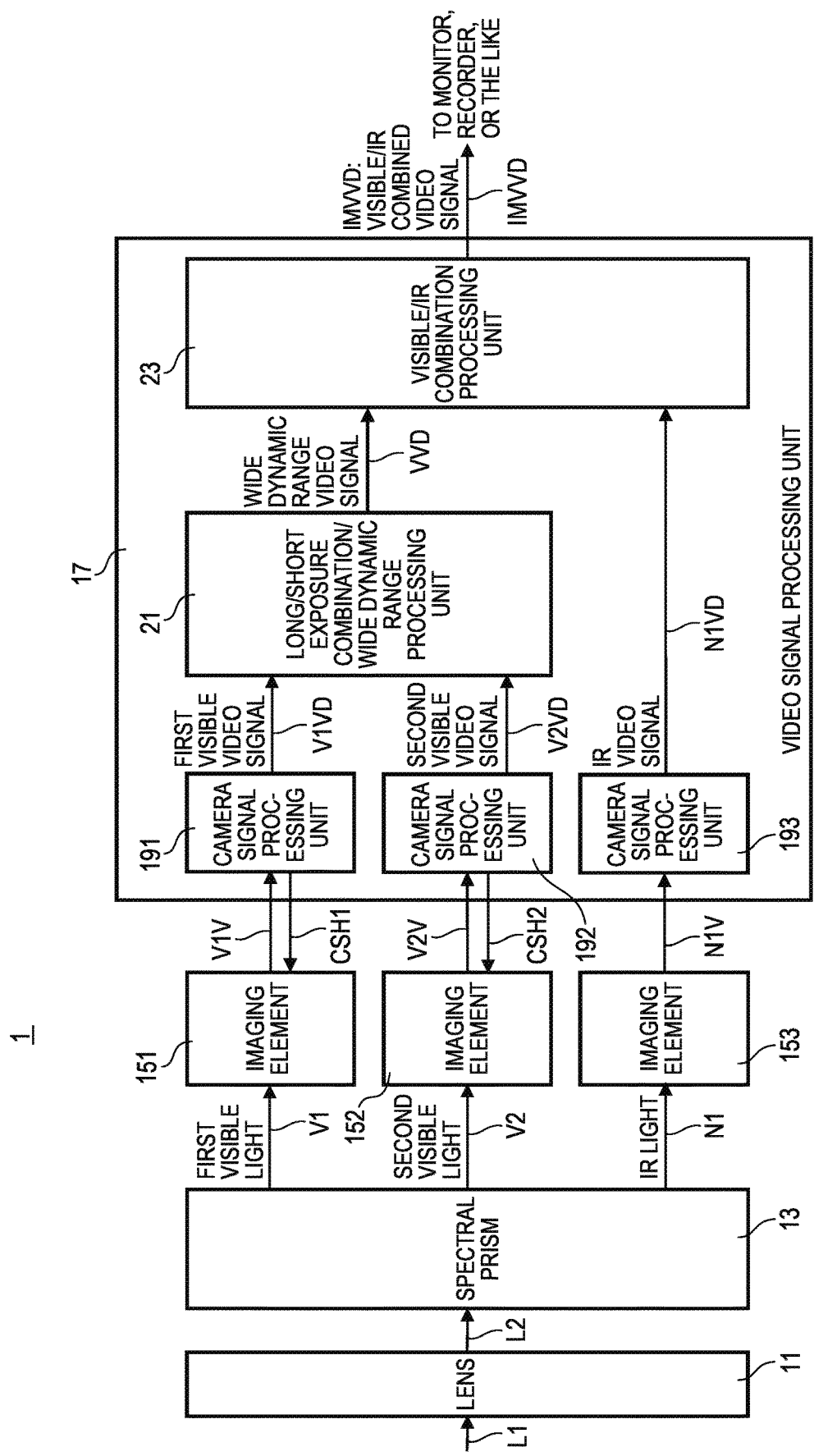
FIG. 1 is a block diagram showing an internal configuration example of a 3 mos camera according to a first embodiment.

FIG. 1 is a block diagram showing an internal configuration example of a 3 mos camera 1 according to a first embodiment. The 3 mos camera 1 is configured to include a lens 11, a spectral prism 13, imaging elements 151, 152, and 153, and a video signal processing unit 17. The video signal processing unit 17 has camera signal processing units 191, 192, and 193, a long/short exposure combination/wide dynamic range processing unit 21, and a visible/IR combination processing unit 23. Each configuration will be described in detail.

The 3 mos cameras 1 and 1A are used in a medical observation system in which excitation light in a predetermined wavelength band (for example, 760 nm to 800 nm) is emitted to a fluorescent reagent (for example, indocyanine green and hereinafter referred to as "ICG") administered in advance to an observation part (for example, diseased part) in a subject such as a patient at the time of, for example, surgery or examination to image the observation part that emits fluorescent light on a long wavelength side (for example, 820 nm to 860 nm) based on the excitation light. Images (for example, videos of the observation part) captured by the 3 mos cameras 1 and 1A are displayed on a monitor MN1 (refer to FIG. 9) and assist a user such as doctor in executing a medical procedure. Spectral prisms 13 and 13A will be described as examples used in the medical observation system described above. However, the use thereof is not limited to medical usage and the prisms may be used for industrial usage.

Figure 2:
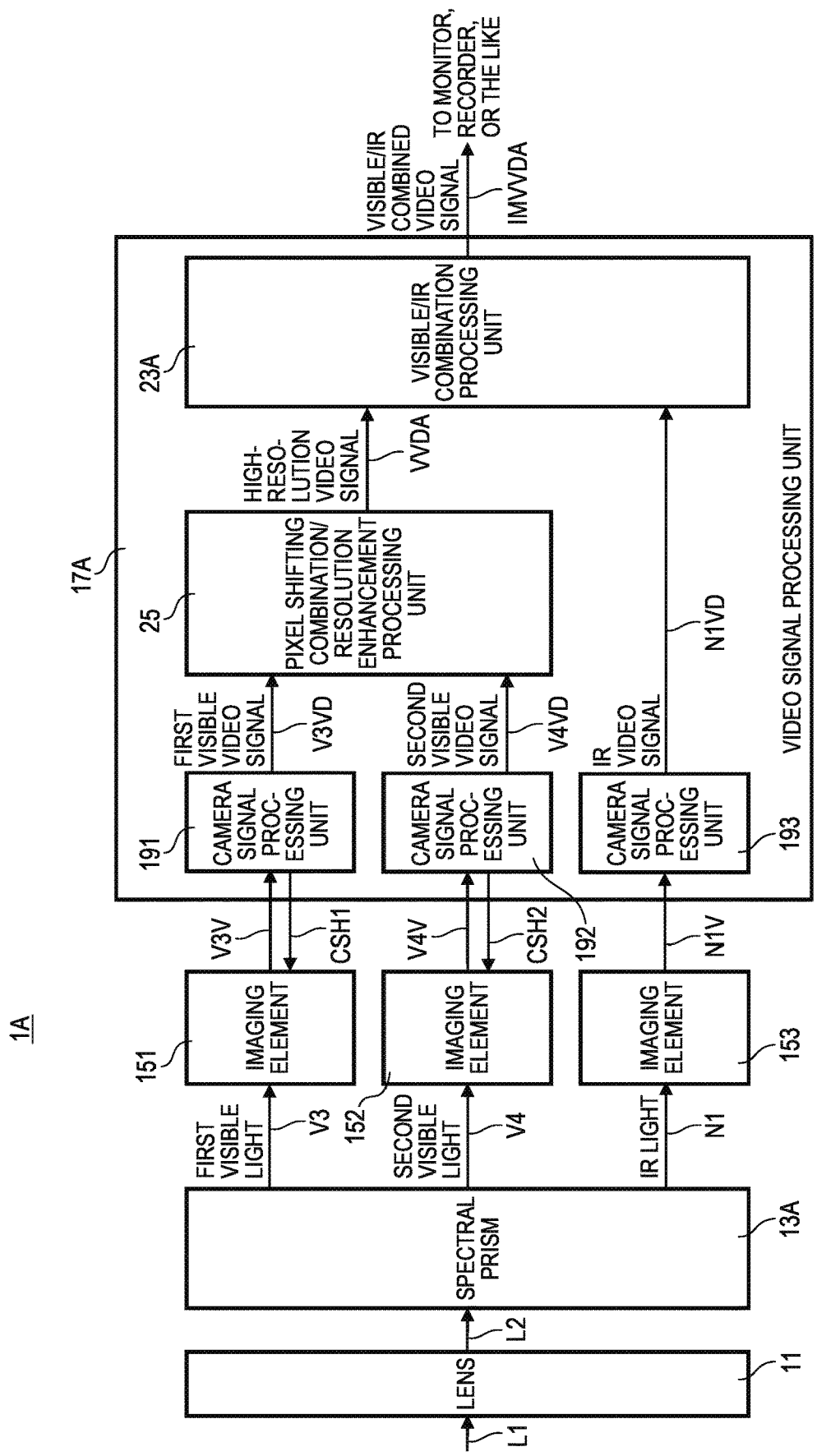
FIG. 2 is a block diagram showing an internal configuration example of a 3 mos camera according to a modification example of the first embodiment.

Although not shown in FIG. 1 or FIG. 2, a tip side of the lens 11 of the 3 mos cameras 1 and 1A is configured of a scope inserted into the observation part (for example, diseased part. The same applies below). This scope is, for example, a main portion of a medical instrument such as a rigid endoscope inserted into the observation part and is an elongated light guide member capable of guiding light L1 from the observation part to the lens 11.

The lens 11 is attached to an objective side (tip side) of the spectral prism 13 and collects the light L1 from the observation part (for example, reflected light at the observation part). Collected light L2 is incident on the spectral prism 13.

The spectral prism 13, which is an example of an optical component, is mounted on the 3 mos camera 1, receives the light L2 from the observation part, and splits the light into first visible light V1, second visible light V2, and IR light N1. The spectral prism 13 has a configuration having an IR prism 31, a visible prism 32, and a visible prism 33 (refer to FIG. 3). The first visible light V1 is incident on the imaging element 151 disposed so as to face the visible prism 32. The second visible light V2 is incident on the imaging element 152 disposed so as to face the visible prism 33. The IR light N1 is incident on the imaging element 153 disposed so as to face the IR prism 31. A detailed structural example of the spectral prism 13 will be described below with reference to FIG. 3.

The imaging element 151 as an example of a second image sensor includes, for example, a charge coupled device (CCD) or a complementary metal oxide semiconductor (CMOS) in which a plurality of pixels suitable for imaging visible light are arranged, and an exposure control circuit (not shown) using an electronic shutter. The imaging element 151 is disposed so as to face the visible prism 32 (refer to FIG. 3). The imaging element 151 captures an image based on the first visible light V1 that is incident for a first exposure time determined by the exposure control circuit based on an exposure control signal CSH1 from the camera signal processing unit 191. The imaging element 151 generates a video signal V1V of the observation part by imaging and outputs the signal to the video signal processing unit 17.

The imaging element 152 as an example of a third image sensor includes, for example, a CCD or a CMOS in which a plurality of pixels suitable for imaging visible light are arranged, and an exposure control circuit (not shown) using an electronic shutter. The imaging element 152 is disposed so as to face the visible prism 33 (refer to FIG. 3). The imaging element 152 captures an image based on the second visible light V2 that is incident for a second exposure time determined by the exposure control circuit based on an exposure control signal CSH2 from the camera signal processing unit 192. The imaging element 152 generates a video signal V2V of the observation part by imaging and outputs the signal to the video signal processing unit 17.

The imaging element 153 as an example of a first image sensor includes, for example, a CCD or a CMOS in which a plurality of pixels suitable for imaging IR light are arranged. The imaging element 153 is disposed so as to face the IR prism 31 (refer to FIG. 3). The imaging element 153 captures an image based on the incident IR light N1. The imaging element 153 generates a video signal N1V of the observation part by imaging and outputs the signal to the video signal processing unit 17.

The video signal processing unit 17 is configured of a processor such as a digital signal processor (DSP) or a field programmable gate array (FPGA). The camera signal processing units 191 to 193, the long/short exposure combination/wide dynamic range processing unit 21, and the visible/IR combination processing unit 23 are executed by the processor described above.

The camera signal processing unit 191 performs various types of camera signal processing using the video signal V1V from the imaging element 151 to generate a first visible video signal V1VD of the observation part, and outputs the signal to the long/short exposure combination/wide dynamic range processing unit 21. The camera signal processing unit 191 generates the exposure control signal CSH1 for determining the first exposure time of the imaging element 151 and outputs the signal to the imaging element 151. The imaging element 151 controls the exposure time of the first visible light V1 based on the exposure control signal CSH1.

The camera signal processing unit 192 performs various types of camera signal processing using the video signal V2V from the imaging element 152 to generate a second visible video signal V2VD of the observation part, and outputs the signal to the long/short exposure combination/wide dynamic range processing unit 21. Although details will be described below, the first visible video signal V1VD and the second visible video signal V2VD have different brightness (sensitivity). The camera signal processing unit 192 generates the exposure control signal CSH2 for determining the exposure time of the imaging element 152 and outputs the signal to the imaging element 152. The imaging element 152 controls the second exposure time of the second visible light V2 based on the exposure control signal CSH2. Although the details will be described below, the first exposure time and the second exposure time may be the same (refer to FIG. 5) or may be different (refer to FIGS. 6, 7, and 8), and the same applies hereinafter.

The camera signal processing unit 193 performs various types of camera signal processing using the video signal N1V from the imaging element 153 to generate an IR video signal N1VD of the observation part, and outputs the signal to the visible/IR combination processing unit 23.

The long/short exposure combination/wide dynamic range processing unit 21 inputs and superimposes two video signals having different brightness (sensitivity) (specifically, the first visible video signal V1VD from the camera signal processing unit 191 and the second visible video signal V2VD from the camera signal processing unit 192) for combining the signals to generate a wide dynamic range video signal VVD. The long/short exposure combination/wide dynamic range processing unit 21 superimposes and combines the two video signals having different brightness (sensitivity) and thus can generate the wide dynamic range video signal VVD with an apparently wider dynamic range than the first visible video signal V1VD or the second visible video signal V2VD. The long/short exposure combination/wide dynamic range processing unit 21 outputs the wide dynamic range video signal VVD to the visible/IR combination processing unit 23.

The visible/IR combination processing unit 23 inputs and superimposes the wide dynamic range video signal VVD from the long/short exposure combination/wide dynamic range processing unit 21 and the IR video signal N1VD from the camera signal processing unit 193 for combining the signals to generate a visible/IR combined video signal IMVVD. The visible/IR combination processing unit 23 may output the visible/IR combined video signal IMVVD to the monitor MN1 or send the signal to a recording device (not shown) for accumulation.

The monitor MN1 constitutes, for example, an image console (not shown) disposed in a surgery room at the time of surgery or examination, and displays the visible/IR combined video signal IMVVD of the observation part generated by the 3 mos camera 1. Accordingly, the user such as doctor can visually recognize the visible/IR combined video signal IMVVD displayed on the monitor MN1 to grasp in detail the part that emits fluorescent light in the observation part. The recording device is a recorder capable of recording data of the visible/IR combined video signal IMVVD generated by the 3 mos camera 1, for example.

FIG. 2 is a block diagram showing an internal configuration example of the 3 mos camera 1A according to a modification example of the first embodiment. In the first embodiment, a light amount of the first visible light V1 incident on the imaging element 151 is different from a light amount of the second visible light V2 incident on the imaging element 152. Therefore, the first visible video signal V1VD from the camera signal processing unit 191 and the second visible video signal V2VD from the camera signal processing unit 192 have different brightness (sensitivity), the first visible video signal V1VD and the second visible video signal V2VD having different brightness (sensitivity) are combined, and thus it is possible to generate the wide dynamic range video signal VVD with an apparently wide dynamic range.

In the modification example of the first embodiment, unlike the first embodiment, a light amount of first visible light V3 incident on the imaging element 151 and a light amount of second visible light V4 incident on the imaging element 152 are substantially equal (in other words, there is not much difference). Therefore, a first visible video signal V3VD from the camera signal processing unit 191 and a second visible video signal V4VD from the camera signal processing unit 192 have substantially the same brightness (sensitivity), combination processing is performed after pixel shifting on one of the first visible video signal V3VD and the second visible video signal V4VD having substantially the same brightness (sensitivity) is performed, and then it is possible to generate a high-resolution video signal VVDA with enhanced resolution. In the description of FIG. 2, the same reference numeral is assigned to the same configuration as that of FIG. 1 to simplify or omit the description, and different contents will be described.

The 3 mos camera 1A is configured to include the lens 11, the spectral prism 13A, the imaging elements 151, 152, and 153, and a video signal processing unit 17A. The video signal processing unit 17A includes the camera signal processing units 191, 192, and 193, a pixel shifting combination/resolution enhancement processing unit 25, and the visible/IR combination processing unit 23. Each configuration will be described in detail. In FIG. 2, the pixel shifting combination/resolution enhancement processing unit 25 is provided instead of the long/short exposure combination/wide dynamic range processing unit 21 in FIG. 1. However, the video signal processing unit 17A may further have the long/short exposure combination/wide dynamic range processing unit 21 shown in FIG. 1. In other words, in FIG. 1, the long/short exposure combination/wide dynamic range processing unit 21 is provided instead of the pixel shifting combination/resolution enhancement processing unit 25 in FIG. 2. However, the video signal processing unit 17 may further have the pixel shifting combination/resolution enhancement processing unit 25 shown in FIG. 2.

The spectral prism 13A is mounted on the 3 mos camera 1A, receives the light L2 from the observation part, and splits the light into the first visible light V3, the second visible light V4, and the IR light N1. The spectral prism 13A has a configuration having the IR prism 31, the visible prism 32, and the visible prism 33 (refer to FIG. 3). The first visible light V3 is incident on the imaging element 151 disposed so as to face the visible prism 32. The second visible light V4 is incident on the imaging element 152 disposed so as to face the visible prism 33. The IR light N1 is incident on the imaging element 153 disposed so as to face the IR prism 31. A detailed structural example of the spectral prism 13A will be described below with reference to FIG. 3.

In the 3 mos camera 1A, the video signal processing unit 17A generates the high-resolution video signal VVDA by pixel shifting. Therefore, in the spectral prism 13A, when the imaging element 151 on which the first visible light V3 is incident and the imaging element 152 on which the second visible light V4 is incident are respectively bonded to the corresponding visible prisms 32 and 33, it is necessary to optically shift positions of the imaging element 151 and the imaging element 152 by about half a pixel (for example, in the horizontal or vertical direction, or in both directions) to perform the bonding. Accordingly, the pixel shifting combination/resolution enhancement processing unit 25 generates the high-resolution video signal VVDA by pixel shifting based on the imaging of the imaging elements 151 and 152 which are disposed in an optically shifted manner by half a pixel (refer to above).

The camera signal processing unit 191 performs the various types of camera signal processing using the video signal V3V from the imaging element 151 to generate the first visible video signal V3VD of the observation part, and outputs the signal to the pixel shifting combination/resolution enhancement processing unit 25. The camera signal processing unit 191 generates the exposure control signal CSH1 for determining the first exposure time of the imaging element 151 and outputs the signal to the imaging element 151. The imaging element 151 controls the exposure time of the first visible light V3 based on the exposure control signal CSH1.

The camera signal processing unit 192 performs the various types of camera signal processing using the video signal V4V from the imaging element 151 to generate the second visible video signal V4VD of the observation part, and outputs the signal to the pixel shifting combination/resolution enhancement processing unit 25. As described above, the first visible video signal V3VD and the second visible video signal V4VD have different brightness (sensitivity). The camera signal processing unit 192 generates the exposure control signal CSH2 for determining the second exposure time of the imaging element 152 and outputs the signal to the imaging element 152. The imaging element 152 controls the exposure time of the second visible light V4 based on the exposure control signal CSH2.

The pixel shifting combination/resolution enhancement processing unit 25 inputs the two video signals (specifically, the first visible video signal V3VD from the camera signal processing unit 191 and the second visible video signal V4VD from the camera signal processing unit 192) having substantially the same brightness (sensitivity). The pixel shifting combination/resolution enhancement processing unit 25 performs the combination processing of the received two input video signals (that is, combination of the first visible video signal V3VD generated by the camera signal processing unit 191 based on the imaging of the imaging element 151 bonded to the visible prism 32 and the second visible video signal V4VD generated by the camera signal processing unit 192 based on the imaging of the imaging element 152 bonded to the visible prism 33) to generate the high-resolution video signal VVDA. The pixel shifting combination/resolution enhancement processing unit 25 performs the combination processing (refer to above) of the received two input video signals and thus can generate the high-resolution video signal VVDA having a higher resolution than the first visible video signal V3VD or the second visible video signal V4VD. The pixel shifting combination/resolution enhancement processing unit 25 outputs the high-resolution video signal VVDA to a visible/IR combination processing unit 23A.

The visible/IR combination processing unit 23A inputs and superimposes the high-resolution video signal VVDA from the pixel shifting combination/resolution enhancement processing unit 25 and the IR video signal N1VD from the camera signal processing unit 193 for combining the signals to generated a visible/IR combined video signal IMVVDA. The visible/IR combination processing unit 23A may output the visible/IR combined video signal IMVVDA to the monitor MN1 or send the signal to a recording device (not shown) for accumulation.

Figure 3:
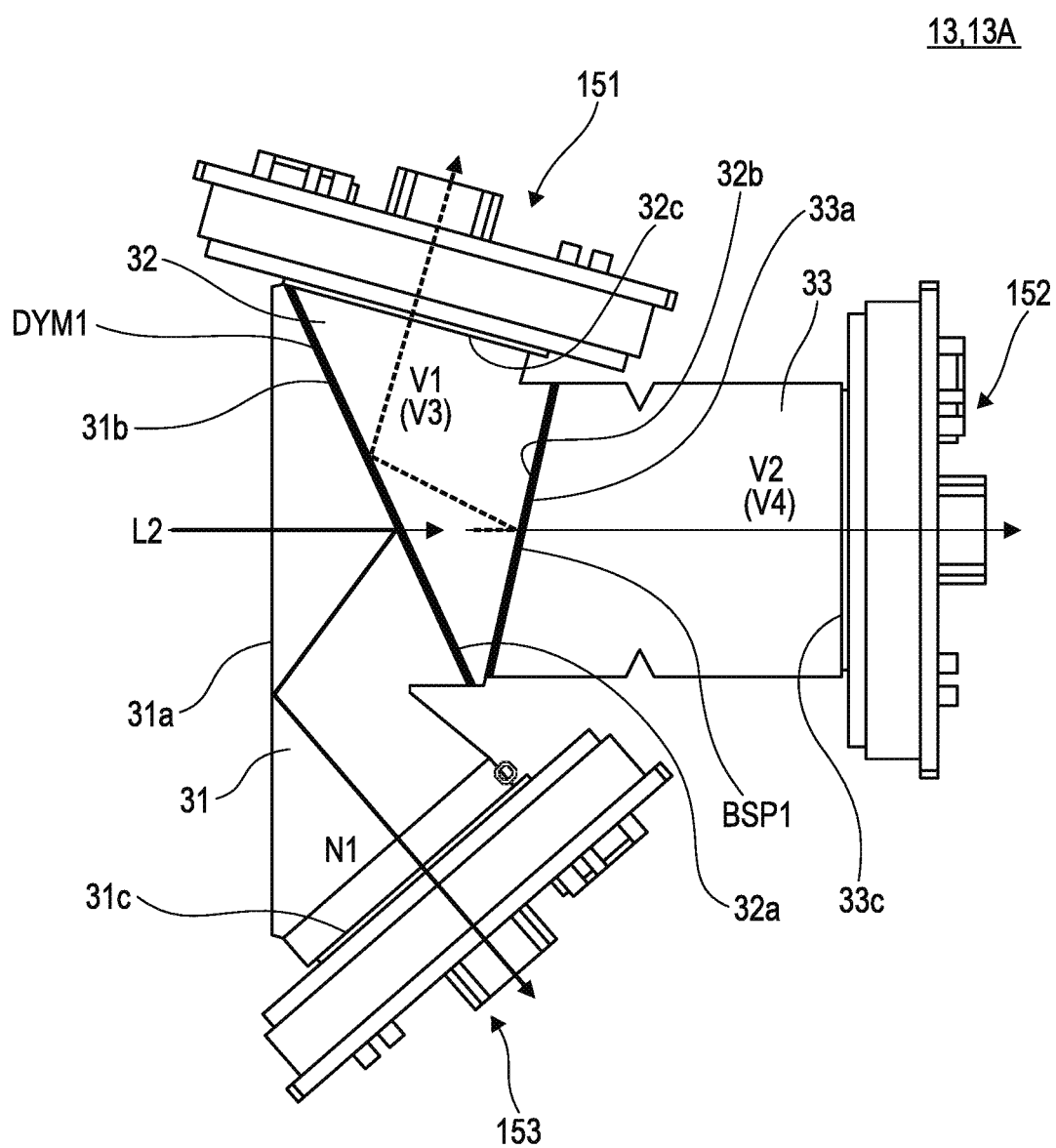
FIG. 3 is a diagram showing a structural example of a spectral prism shown in FIG. 1 or FIG. 2.

FIG. 3 is a diagram showing a structural example of the spectral prisms 13 and 13A shown in FIG. 1 or FIG. 2. Hereinafter, the structural example of the spectral prism 13 shown in FIG. 1 will be mainly described with reference to FIG. 3, and the description of the spectral prism 13A shown in FIG. 2 will be described with supplement as appropriate. That is, as the description of the spectral prism 13A shown in FIG. 2, description of contents overlapping the description of the spectral prism 13 shown in FIG. 1 below will be omitted, and description specific to the spectral prism 13A will be separately supplemented.

The spectral prism 13 includes the IR prism 31 (an example of a first prism), the visible prism 32 (an example of a second prism), and the visible prism 33 (an example of a third prism). The IR prism 31, the visible prism 32, and the visible prism 33 are sequentially assembled in an optical axis direction of the light L2 collected by the lens 11.

The IR prism 31 as an example of the first prism includes an incident surface 31a on which the light L2 is incident, a reflection surface 31b on which a dichroic mirror DYM1 that reflects the IR light of the light L2 is formed, and an emission surface 31c from which the IR light is emitted. The dichroic mirror DYM1 (an example of first reflection film) is formed on the reflection surface 31b by vapor deposition or the like, reflects the IR light (for example, IR light in the wavelength band of 800 nm or more) of the light L2, and transmits light (for example, light of about 400 nm to 800 nm) other than the IR light of the light L2 (refer to FIG. 4A). Specifically, the IR light (refer to above) of the light L2 incident on the incident surface 31a of the IR prism 31 is reflected by the reflection surface 31b. This IR light is reflected by the reflection surface 31b, is then totally reflected by the incident surface 31a of the IR prism 31, and is incident on the imaging element 153 through the emission surface 31c.

Figure 4A:
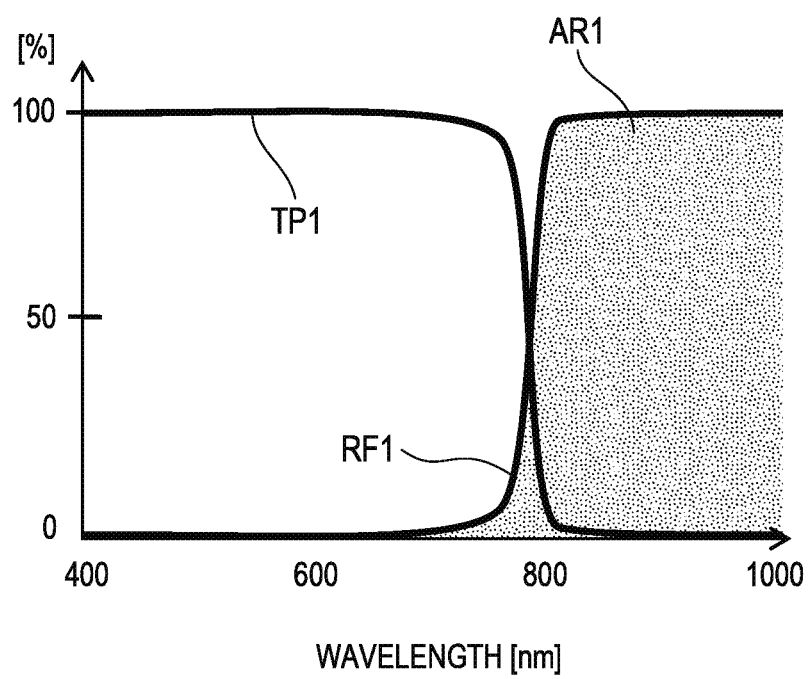
FIG. 4A is a graph showing an example of spectral characteristics of a dichroic mirror.

FIG. 4A is a graph showing an example of spectral characteristics of the dichroic mirror DYM1. The horizontal axis of FIG. 4A indicates wavelength [nm: nanometer (the same applies below)], and the vertical axis indicates reflectance or transmittance. A characteristic TP1 indicates the transmittance of the dichroic mirror DYM1. According to the characteristic TP1, the dichroic mirror DYM1 can transmit the light of about 400 nm to 800 nm. A characteristic RF1 indicates the reflectance of the dichroic mirror DYM1. According to the characteristic RF1, the dichroic mirror DYM1 can reflect the IR light of 800 nm or more. Therefore, all the IR light having a light amount indicated by an area AR1 (in other words, the IR light of the light L2) can be incident on the imaging element 153.

The visible prism 32 as an example of the second prism includes an incident surface 32a on which the light (an example of first transmitted light) transmitted through the dichroic mirror DYM1 is incident, a reflection surface 32b on which a beam splitter BSP1 for reflecting a partial light amount of the transmitted light (an example of light in a specific wavelength band) is formed, and an emission surface 32c from which reflected visible light of the partial light amount is emitted. The beam splitter BSP1 (an example of second reflection film) is formed on the reflection surface 32b by vapor deposition or the like, reflects visible light having a partial light amount (for example, about 10% of the light incident on the incident surface 32a) of the visible light incident on the incident surface 32a, and transmits visible light having a remaining light amount (for example, about 90% of the light incident on the incident surface 32a) thereof (refer to FIG. 4B). Specifically, the visible light having the partial light amount (for example, 10%) of the visible light incident on the incident surface 32a of the visible prism 32 is reflected by the reflection surface 32b. This part of the visible light is reflected by the reflection surface 32b, is then totally reflected by the incident surface 32a of the visible prism 32, and is incident on the imaging element 151 through the emission surface 32c. In the spectral prism 13 shown in FIG. 1, the ratio of visible light reflected by the beam splitter BSP1 is not limited to 10% and may be in a range of 5% to 30%, for example.

Figure 4B:
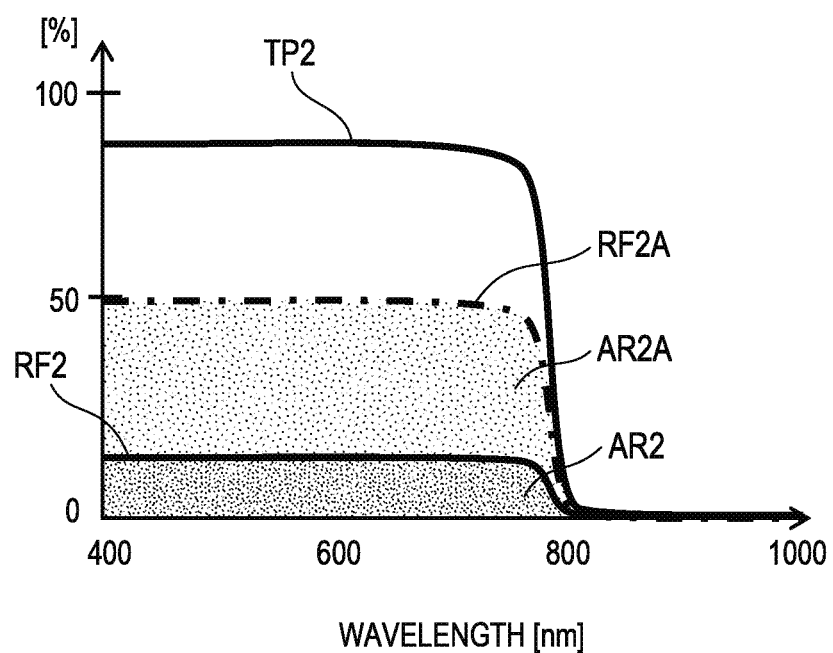
FIG. 4B is a graph showing an example of spectral characteristics of a beam splitter.

In the case of the spectral prism 13A shown in FIG. 2, the beam splitter BSP1 (an example of the second reflection film) reflects visible light having a partial light amount (for example, about 50% of the light incident on the incident surface 32a) of the visible light incident on the incident surface 32a and transmits visible light having a remaining light amount (for example, about 50% of the light incident on the incident surface 32a) thereof (refer to FIG. 4B). In the spectral prism 13A shown in FIG. 2, the ratio of visible light reflected by the beam splitter BSP1 is not limited to 50%, and may be in a range of 30% to 50%, for example.

The visible prism 33 as an example of the third prism has an incident surface 33a on which the visible light having the remaining light amount transmitted through the beam splitter BSP1 is incident and an emission surface 33c from which the visible light having the remaining light amount is emitted. Specifically, the visible light having the remaining light amount transmitted through the beam splitter BSP1 is incident on the visible prism 33, is emitted as it is, and is incident on the imaging element 152 (refer to FIG. 4C).

Figure 4C:
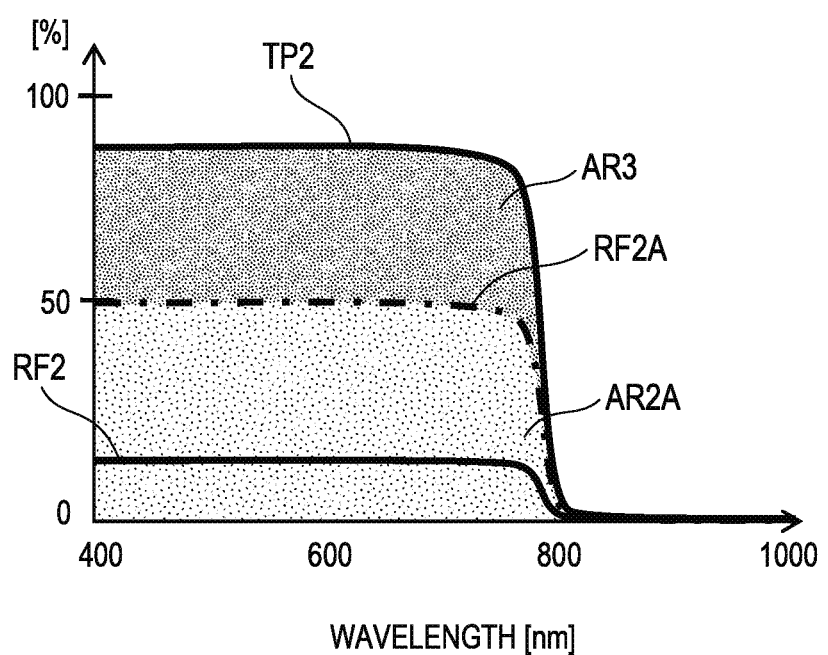
FIG. 4C is a graph showing an example of spectral characteristics of the beam splitter.

FIGS. 4B and 4C are graphs showing examples of spectral characteristics of the beam splitter BSP1. In FIGS. 4B and 4C, the horizontal axis indicates wavelength [nm] and the vertical axis indicates reflectance or transmittance. A characteristic TP2 indicates the transmittance (about 90% at 400 nm to 800 nm) of the beam splitter BSP1 in the spectral prism 13 shown in FIG. 1, and a characteristic RF2 indicates the reflectance (about 10% at 400 nm to 800 nm) of the beam splitter BSP1 in the spectral prism 13 shown in FIG. 1. According to the characteristic TP2 and the characteristic RF2, the beam splitter BSP1 as an example of the second reflection film can reflect light having a light amount of about 10% (mainly visible light) of the light of about 400 nm to 800 nm and can transmit light having a remaining light amount of about 90% (mainly visible light) thereof. Therefore, visible light having a light amount indicated by an area AR2 (for example, visible light having light amount of about 10%) can be incident on the imaging element 151. The transmittance of 90% and the reflectance of 10% are merely examples, and the numerical values are not limited to the values.

A characteristic RF2A indicates the transmittance and reflectance (about 50% at 400 nm to 800 nm) of the beam splitter BSP1 in the spectral prism 13A shown in FIG. 2. According to the characteristic RF2A, the beam splitter BSP1 as an example of the second reflection film can reflect visible light having a light amount of about 50% of the visible light of about 400 nm to 800 nm and can transmit visible light having a remaining light amount of about 50% thereof. Therefore, visible light having a light amount indicated by an area AR2A (for example, visible light having light amount of about 50%) can be incident on the imaging element 151. The transmittance and the reflectance of 50% are merely examples, and the numerical values are not limited to the values.

As shown in FIG. 4C, the beam splitter BSP1 can reflect visible light having a light amount of about 10% of the visible light of about 400 nm to 800 nm and can transmit visible light having a remaining light amount of about 90% thereof. Visible light having a light amount indicated by an area AR3 (for example, visible light having light amount of about 90%) can be incident on the imaging element 152. Visible light having a light amount indicated by an area AR2A (for example, visible light having light amount of about 50%) can be incident on the imaging element 152.

Figure 5:
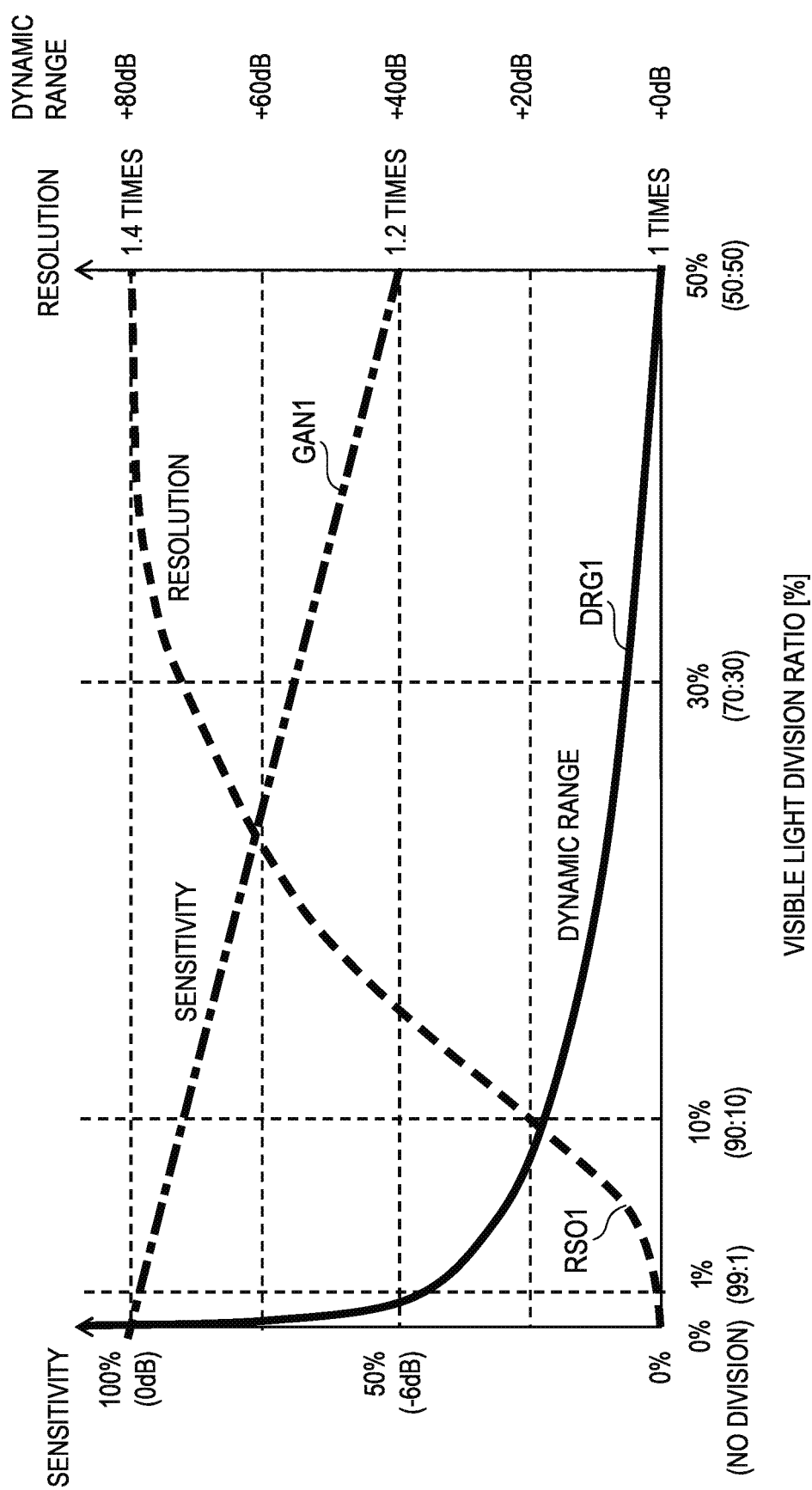
FIG. 5 is a graph showing an example of a relationship between visible light division ratio and sensitivity, dynamic range, and resolution in a case where exposure times of second visible light and first visible light are the same.

FIG. 5 is a graph showing an example of a relationship between visible light division ratio and sensitivity GAN1, dynamic range DRG1, and resolution RSO1 in a case where exposure times of the second visible light V2 and the first visible light V1 are the same. The horizontal axis of FIG. 5 is the visible light division ratio. In other words, the visible light division ratio is a ratio at which the beam splitter BSP1 reflects the light transmitted through the dichroic mirror DYM1 (that is, visible light). For example, in a case where the visible light division ratio is 10% (that is, 90:10), the beam splitter BSP1 reflects 10% of the visible light transmitted through the dichroic mirror DYM1 and transmits 90% of the visible light. That is, light amount of the second visible light V2:light amount of the first visible light V1 is 90:10. Another visible light division ratio can be considered in the same manner as the specific example described above. The vertical axis of FIG. 5 represents the sensitivity GAN1, the dynamic range DRG1, and the resolution RSO1 of the wide dynamic range video signal VVD or the high-resolution video signal VVDA generated in the video signal processing units 17 and 17A, respectively.

FIG. 5 shows an example in which the exposure times for the imaging elements 152 and 151 by the electronic shutter are controlled to be the same. Therefore, it is considered that the sensitivity GAN1 transitions according to a characteristic (for example, a linear function) that the sensitivity is the maximum as the visible light division ratio is smaller (for example, the maximum (100%) and the brightest when the ratio is 0%) and the sensitivity is the minimum (for example, the darkest at 50%) when the ratio is 50%. This is because the sensitivity is determined by the brightness of the brighter second visible light V2 of the brightness of the first visible video signal V1VD based on the first visible light V1 and the brightness of the second visible video signal V2VD based on the second visible light V2.

It is considered that the dynamic range DRG1 transitions according to a characteristic that the dynamic range increases similarly as the visible light division ratio is smaller in a range larger than zero (for example, about +80 dB when the ratio is 0.01%) and the dynamic range is the minimum (for example, 0 dB) when the ratio is 50%. This is because a difference between a dark portion and a bright portion tends to widen as the visible light division ratio is smaller in the wide dynamic range video signal VVD or the high-resolution video signal VVDA.

It is considered that the resolution RSO1 transitions according to a characteristic that the resolution is the minimum contrarily as the visible light division ratio is smaller (for example, the maximum of 1 time when the ratio is 0%) and the resolution is the maximum (for example, 1.4 times) when the ratio is 50%. This is because a difference in pixel value between adjacent pixels is small as the visible light division ratio is larger and thus it is easy to realize high resolution by pixel shifting.

Figure 6:
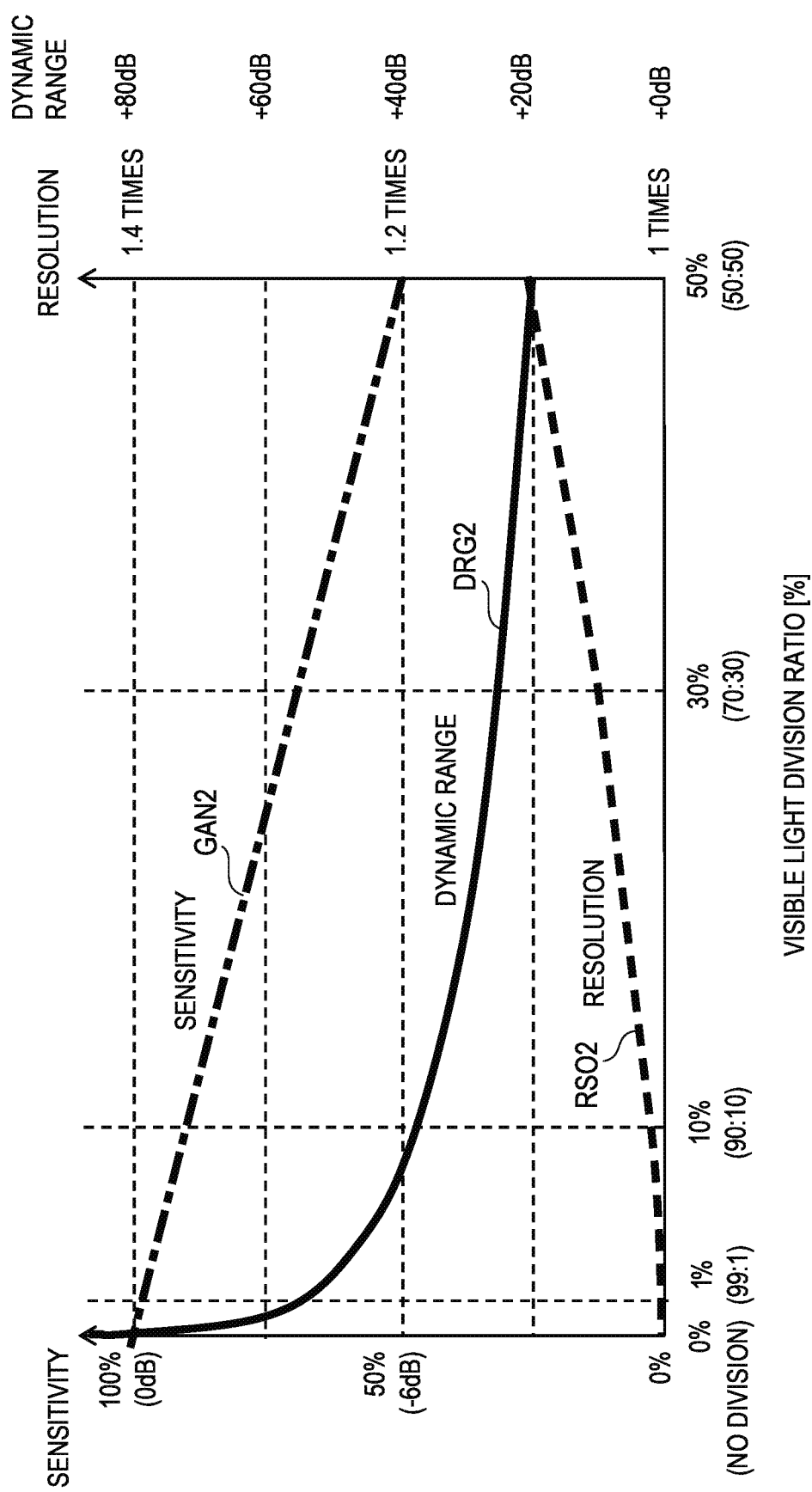
FIG. 6 is a graph showing an example of the relationship between visible light division ratio and sensitivity, dynamic range, and resolution in a case where a ratio of the exposure times of the second visible light and the first visible light is 10:1.

FIG. 6 is a graph showing an example of a relationship between visible light division ratio and sensitivity GAN2, dynamic range DRG2, and resolution RSO2 in a case where a ratio of the exposure times of the second visible light V2 and the first visible light V1 is 10:1. The horizontal axis of FIG. 6 is the visible light division ratio, and description thereof will be omitted since the description is the same as that in FIG. 5. The vertical axis of FIG. 6 represents the sensitivity GAN2, the dynamic range DRG2, and the resolution RSO2 of the wide dynamic range video signal VVD or the high-resolution video signal VVDA generated in the video signal processing units 17 and 17A, respectively.

FIG. 6 shows an example in which a difference is provided such that a ratio of the exposure times for the imaging elements 152 and 151 by the electronic shutter is 10:1. It is considered, as in the case of the sensitivity GAN1 shown in FIG. 5, that the sensitivity GAN2 transitions according to a characteristic (for example, a linear function) that the sensitivity is the maximum as the visible light division ratio is smaller (for example, the maximum (100%) and the brightest when the ratio is 0%) and the sensitivity is the minimum (for example, the darkest at 50%) when the ratio is 50%. This is because a brightness ratio of the second visible video signal V2VD and the first visible video signal V1VD is obtained by multiplying the ratio of the exposure times for the imaging elements 152 and 151 of 10:1 by a light amount ratio of the second visible light V2 and the first visible light V1, and the sensitivity is determined by the brightness of the brighter second visible video signal V2VD of the second visible video signal V2VD than the brightness of the first visible video signal V1VD.

When a difference is provided such that the ratio of the exposure times for the imaging elements 152 and 151 is, for example, 10:1 as compared with when the exposure time thereof is the same, it is considered that the difference between the bright portion and the dark portion is likely to appear further clearly and thus it is possible to gain more dynamic range, in the wide dynamic range video signal VVD or the high-resolution video signal VVDA. Therefore, it is considered that the dynamic range DRG2 transitions according to a characteristic that the dynamic range increases similarly as the visible light division ratio is smaller in a range larger than zero (for example, about +80 dB when the ratio is 0.1%) and the dynamic range is the minimum (for example, +20 dB) when the ratio is 50%. That is, it is possible to gain +20 dB even with a minimum value in the example of FIG. 6.

When the difference is provided such that the ratio of the exposure times for the imaging elements 152 and 151 by the electronic shutter is 10:1, it is considered that light amount of light incident on the imaging element 152:light amount of light incident on the imaging element 151=100:1 in a case where the visible light division ratio is 10% (second visible light V2:first visible light V1=90:10). That is, the dark portion is hardly projected by the first visible light V1 and the bright portion is hardly projected by the second visible light V2, and thus it can be considered that it is almost difficult to gain a resolution when two video signals are superimposed. Therefore, it is considered that the resolution RSO2 transitions over small values (for example, the minimum of 1 time at 0%, and about 1.1 times at 50%) regardless of the visible light division ratio.

Figure 7:
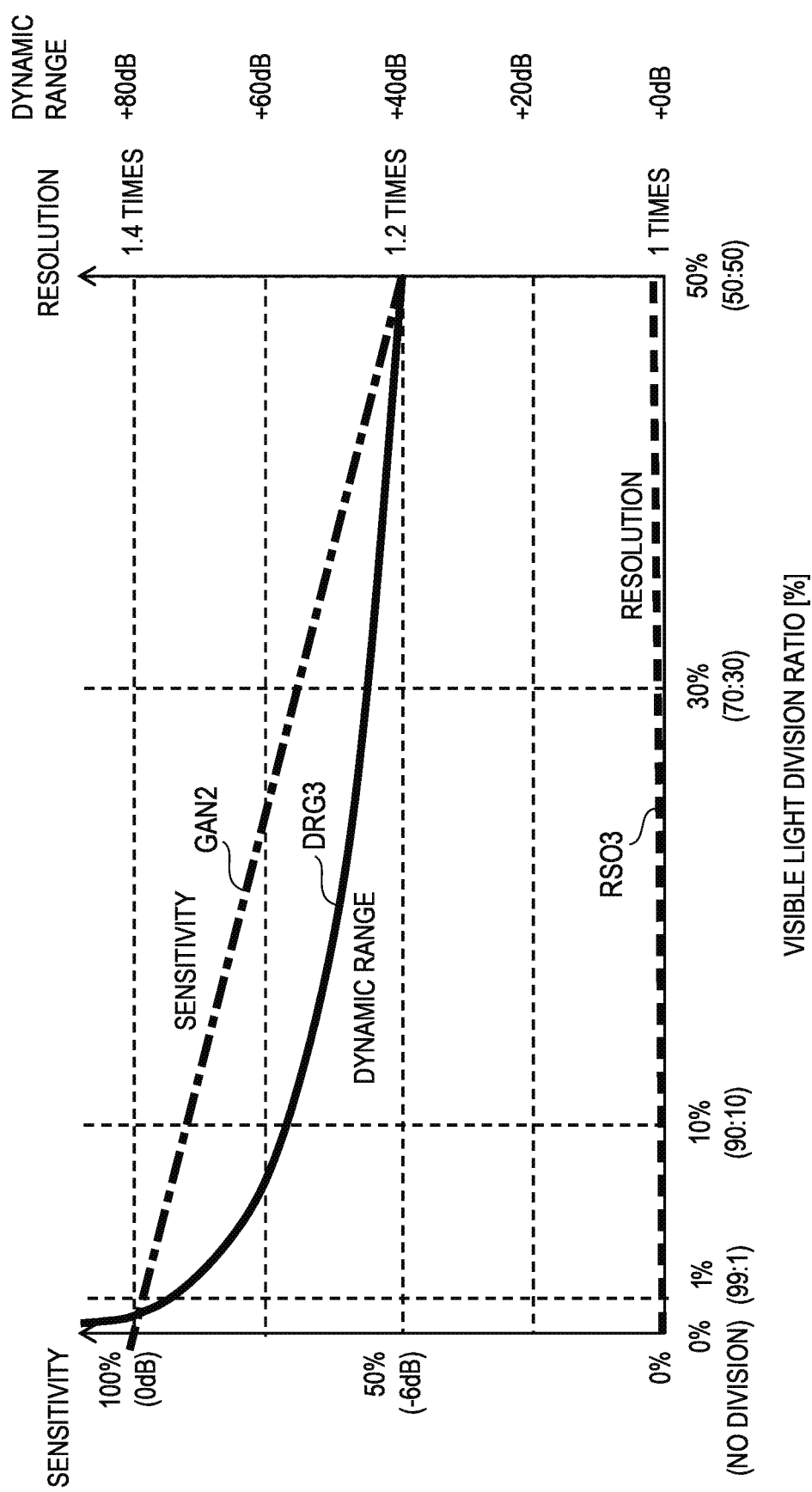
FIG. 7 is a graph showing an example of the relationship between visible light division ratio and sensitivity, dynamic range, and resolution in a case where the ratio of the exposure times of the second visible light and the first visible light is 100:1.

FIG. 7 is a graph showing an example of a relationship between visible light division ratio and sensitivity GAN2, dynamic range DRG3, and resolution RSO3 in a case where the ratio of the exposure times of the second visible light V2 and the first visible light V1 is 100:1. The horizontal axis of FIG. 7 is the visible light division ratio, and description thereof will be omitted since the description is the same as that in FIG. 5. The vertical axis of FIG. 7 represents the sensitivity GAN2, the dynamic range DRG3, and the resolution RSO3 of the wide dynamic range video signal VVD or the high-resolution video signal VVDA generated in the video signal processing units 17 and 17A, respectively.

FIG. 7 shows an example in which a considerable difference is provided such that the ratio of the exposure times for the imaging elements 152 and 151 by the electronic shutter is 100:1. It is considered, as in the case of the sensitivity GAN2 shown in FIG. 6, that the sensitivity GAN2 transitions according to a characteristic (for example, a linear function) that the sensitivity is the maximum as the visible light division ratio is smaller (for example, the maximum (100%) and the brightest when the ratio is 0%) and the sensitivity is the minimum (for example, the darkest at 50%) when the ratio is 50%. This is because a brightness ratio of the second visible video signal V2VD and the first visible video signal V1VD is obtained by multiplying the ratio of the exposure times for the imaging elements 152 and 151 of 100:1 by a light amount ratio of the second visible light V2 and the first visible light V1, and the sensitivity is determined by the brightness of the brighter second visible video signal V2VD of the second visible video signal V2VD than the brightness of the first visible video signal V1VD.

When a considerable difference is provided such that the ratio of the exposure times for the imaging elements 152 and 151 is, for example, 100:1 as compared with when the exposure time thereof is the same, it is considered that the difference between the bright portion and the dark portion is likely to appear furthermore clearly and thus it is possible to gain more dynamic range, in the wide dynamic range video signal VVD or the high-resolution video signal VVDA. Therefore, it is considered that the dynamic range DRG3 transitions according to a characteristic that the dynamic range increases similarly as the visible light division ratio is smaller in a range larger than zero (for example, about +80 dB when the ratio is 1%) and the dynamic range is the minimum (for example, +40 dB) when the ratio is 50%. That is, it is possible to gain +40 dB even with a minimum value in the example of FIG. 7.

When the difference is provided such that the ratio of the exposure times for the imaging elements 152 and 151 by the electronic shutter is 100:1, it is considered that light amount of light incident on the imaging element 152:light amount of light incident on the imaging element 151=1000:1 in the case where the visible light division ratio is 10% (second visible light V2:first visible light V1=90:10). That is, the dark portion is hardly projected since the second visible light V2 is too bright and the bright portion is hardly projected since the first visible light V1 is too dark, and thus it can be considered that it is almost difficult to gain a resolution when two video signals are superimposed as compared with the example of FIG. 6. Therefore, it is considered that the resolution RSO3 transitions over small values (for example, the minimum of 1 time at 0% and about 1.02 times at 50%) regardless of the visible light division ratio.

Figure 8:
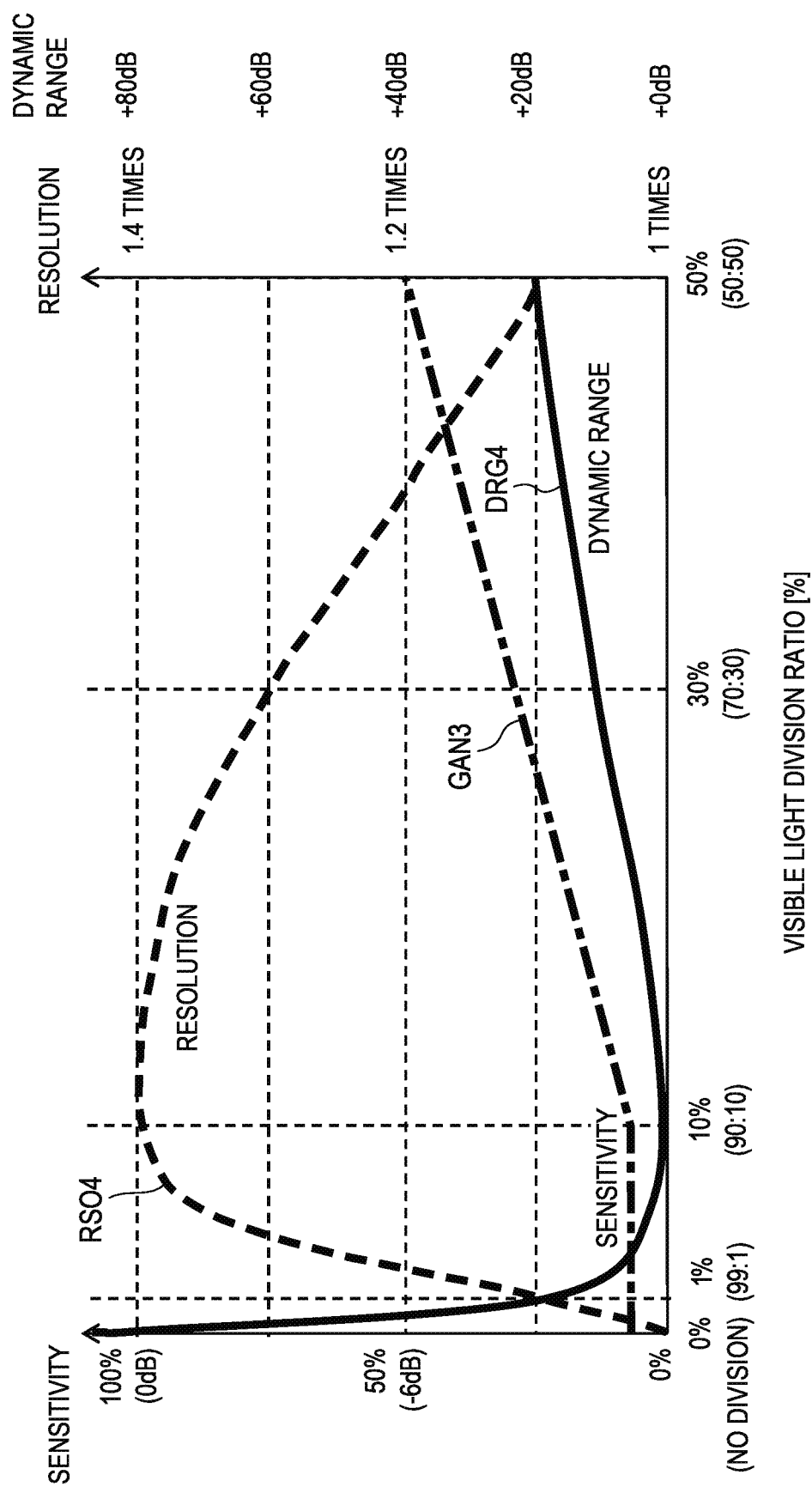
FIG. 8 is a graph showing an example of the relationship between visible light division ratio and sensitivity, dynamic range, and resolution in a case where the ratio of the exposure times of the second visible light and the first visible light is 1:10.

FIG. 8 is a graph showing an example of a relationship between visible light division ratio and sensitivity GAN3, dynamic range DRG4, and resolution RSO4 in a case where the ratio of the exposure times of the second visible light V2 and the first visible light V1 is 1:10. The horizontal axis of FIG. 8 is the visible light division ratio, and description thereof will be omitted since the description is the same as that in FIG. 5. The vertical axis of FIG. 8 represents the sensitivity GAN3, the dynamic range DRG4, and the resolution RSO4 of the wide dynamic range video signal VVD or the high-resolution video signal VVDA generated in the video signal processing units 17 and 17A, respectively.

FIG. 8 shows an example in which a difference is provided such that the ratio of the exposure times for the imaging elements 152 and 151 by the electronic shutter is 1:10. Contrary to the example of FIG. 6, when the difference is provided such that the ratio of the exposure times for the imaging elements 152 and 151 is, for example, 1:10, it is considered that the light amount of light incident on the imaging element 152 and the light amount of light incident on the imaging element 151 are substantially equal due to cancellation of the visible light division ratio and the exposure time ratio in the case where the visible light division ratio is 10% (second visible light V2:first visible light V1=90:10), for example. Therefore, it is considered that the sensitivity GAN3 transitions according to a characteristic that the sensitivity transitions substantially constant so as to be the minimum when the visible light division ratio is from 0% to 10% (in other words, in a case where light amounts incident on the imaging elements 152 and 151 do not change much) and the sensitivity increases monotonically in a linear function until the visible light division ratio is larger than 10% and reaches 50%. For example, the brightness is the maximum (50%, that is, −6 dB) when the visible light division ratio is 50%. This is because a brightness ratio of the second visible video signal V2VD and the first visible video signal V1VD is obtained by multiplying the ratio of the exposure times for the imaging elements 152 and 151 of 1:10 by a light amount ratio of the second visible light V2 and the first visible light V1, and the sensitivity is determined by the brightness of a brighter video signal of the second visible video signal V2VD than the brightness of the first visible video signal V1VD.

When a difference is provided such that the ratio of the exposure times for the imaging elements 152 and 151 is, for example, 1:10 as compared with when the exposure time thereof is the same, it is considered that the difference in brightness is easier to obtain as the visible light division ratio is smaller in a range larger than 0%, but the difference between the bright portion and the dark portion is less likely to appear as the visible light division ratio is higher, and thus it is difficult to gain more dynamic range, in the wide dynamic range video signal VVD or the high-resolution video signal VVDA. Therefore, the dynamic range DRG4 increases as the visible light division ratio is smaller in a range larger than 0% (for example, about +80 dB at 0.001%). However, when the visible light division ratio is 10%, the brightness of the second visible video signal V2VD and the brightness of the first visible video signal V1VD are substantially equal due to the cancellation of the visible light division ratio and the ratio of the exposure times for the imaging elements 152 and 151 of 1:10 and the dynamic range DRG4 is the minimum. When the visible light division ratio exceeds 10%, the brightness of the second visible video signal V2VD is different again from the brightness of the first visible video signal V1VD and the dynamic range DRG4 is large. When the visible light division ratio is 50%, the ratio of the brightness of the second visible video signal V2VD and the brightness of the first visible video signal V1VD is 1:10 by the multiplication of the ratio of the exposure times for the imaging elements 152 and 151 of 1:10 and the dynamic range is +20 dB.

When the difference is provided such that the ratio of the exposure times for the imaging elements 152 and 151 by the electronic shutter is 1:10, it is considered that the light amount of light incident on the imaging element 152 and the light amount of light incident on the imaging element 151 are substantially equal in the case where the visible light division ratio is 10% (second visible light V2:first visible light V1=90:10), for example (refer to above). That is, when the cancellation of the visible light division ratio and the exposure time ratio (1:10) occurs (for example, when the visible light division ratio is 10%), the first visible video signal V1VD based on the first visible light V1 and the second visible video signal V2VD based on the second visible light V2 have the same brightness. Therefore, it is considered that the resolution RSO4 transitions according to a characteristic that the resolution is the maximum and the resolution decreases from the maximum value at a visible light division ratio at which the cancellation is less likely to occur.

Figure 9:
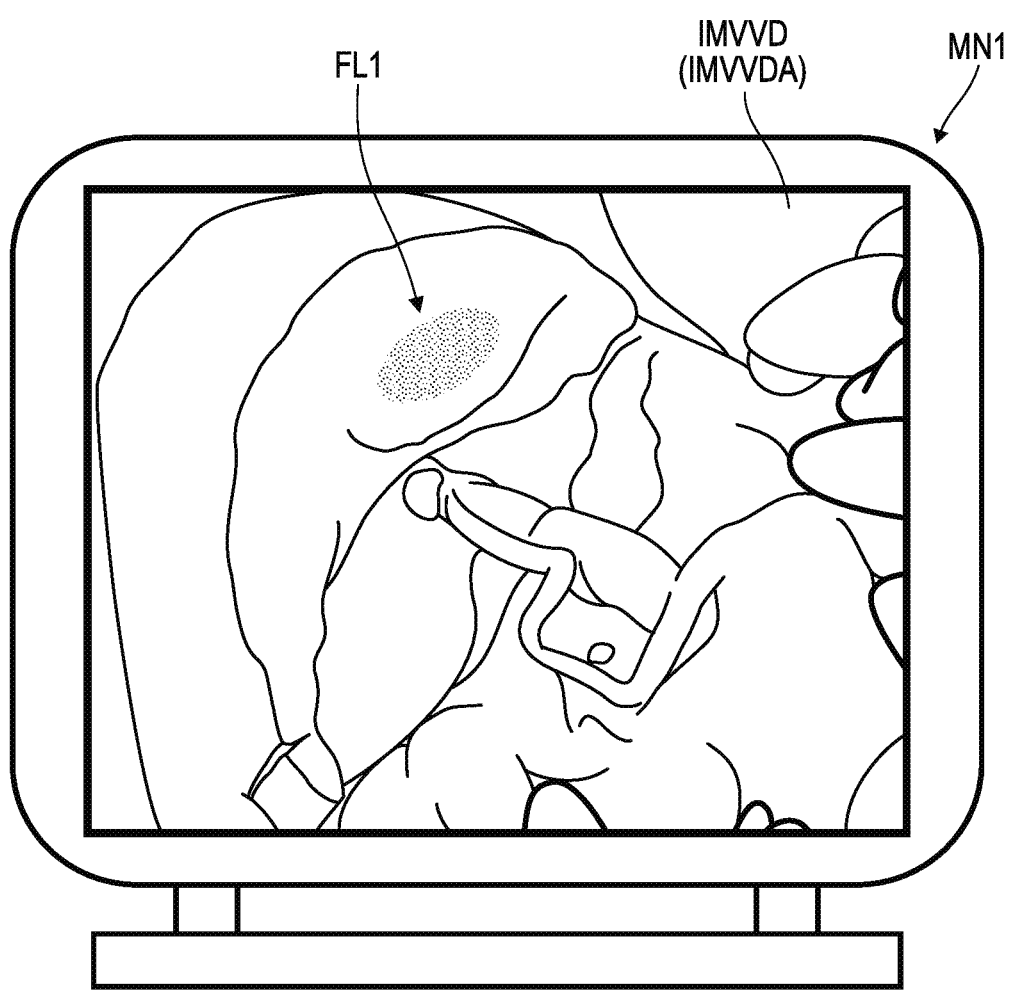
FIG. 9 is a diagram showing a display example of a visible/IR combined video signal generated by the 3 mos camera according to the first embodiment on a monitor.

FIG. 9 is a diagram showing a display example of the visible/IR combined video signals IMVVD and IMVDDA generated by the 3 mos cameras 1 and 1A according to the first embodiment on the monitor MN1. The visible/IR combined video signals IMVVD and IMVDDA shown in FIG. 9 are generated based on imaging at the observation part (for example, around liver and pancreas) of a patient who is the subject and are displayed on the monitor MN1. In FIG. 9, the fluorescent reagent of ICC, which is administered in advance to the diseased part in a body of the patient before operation or examination, emits light, and a place that emits the light (for example, diseased part FL1) is shown so as to be known in the visible/IR combined video signals IMVVD and IMVDDA. In this manner, the 3 mos cameras 1 and 1A generate high-quality visible/IR combined video signals IMVVD and IMVDDA that allow the user such as doctor to grasp the details of the observation part at the time of, for example, surgery or examination, and display the signals on the monitor MN1.

As described above, the 3 mos camera 1 and 1A according to the first embodiment includes the IR prism 31 in which the dichroic mirror DYM1 that reflects the IR light of the light from the observation part (for example, diseased part in the subject) is formed and that causes the imaging element 153 to receive the IR light, the visible prism 32 in which the beam splitter BSP1 that reflects specific wavelength band light (for example, band of 800 nm or more) of the first transmitted light transmitted through the dichroic mirror DYM1 and transmits the visible light is formed and that causes the imaging element 151 to receive the specific wavelength band light described above, and the visible prism 33 that causes the imaging element 152 to receive the visible light transmitted through the beam splitter BSP1. The 3 mos cameras 1 and 1A includes the video signal processing unit 17 that generates a first video signal (IR light N1), a second video signal (first visible light V1), and a third video signal (second visible light V2) of the observation part based on the imaging output of each of the imaging elements 153, 151 and 152, combines the first video signal, the second video signal, and the third video signal, and outputs the combined signal to the monitor MN1.

Accordingly, the 3 mos cameras 1 and 1A can separate (spectralize), by the spectral prisms 13 and 13A, the IR light specialized in the specific wavelength band (for example, 800 nm or more) of the light from the observation part (for example, diseased part) to which the fluorescent reagent (for example, ICG) is administered in advance in the patient at the time of, for example, surgery or examination, that is, in a fluorescent region of the fluorescent reagent. Further, the 3 mos cameras 1 and 1A reflect a part of the visible light other than the specific wavelength band described above of the light from the observation part at the beam splitter BSP1 and transmit the remaining visible light to generate and combine the video signals based on the visible light in two channels (in other words, two imaging elements 151 and 152). Therefore, it is possible to generate a high-quality visible light video signal in terms of sensitivity, dynamic range, or resolution. Therefore, the 3 mos cameras 1 and 1A can generate and output clearer fluorescence images in both IR light and visible light and can assist a doctor or the like in easily grasping the diseased part.

In the 3 mos camera 1 (refer to FIGS. 1 and 4A), the specific wavelength band light is visible light. The beam splitter BSP1 reflects A (A: a predetermined real number) % (for example, 10%) of the visible light that is light transmitted through the dichroic mirror DYM1 and transmits remaining (100−A) % (for example, 90%) of the visible light. A value of A is smaller than a value of (100−A). Accordingly, the 3 mos camera 1 superimposes and combines the two video signals having different brightness (specifically, the first visible video signal V1VD based on the first visible light V1 and the second visible video signal V2VD based on the second visible light V2) and thus can generate the wide dynamic range video signal VVD having high sensitivity and wide dynamic range.

The 3 mos camera 1 combines the second video signal and the third video signal having different brightness to generate a fifth video signal (for example, wide dynamic range video signal VVD) and outputs the video signal (for example, visible/R combined video signal IMVVD) obtained by combining the fifth video signal and the first video signal (for example, IR video signal N1VD) to the monitor MN1. Accordingly, the 3 mos camera 1 can output, to the monitor MN1, a high-quality video signal obtained by superimposing, for example, the IR video signal N1VD capable of discriminating the details of the fluorescent light emitting part of the diseased part on the wide dynamic range video signal VVD having high sensitivity and wide dynamic range based on the two video signals having different brightness.

The 3 mos camera 1 controls the ratio of the exposure times of the imaging elements 151 and 152 to be the same or different. Accordingly, the 3 mos camera 1 can generate high-quality video signals that adaptively realize sensitivity, dynamic range, and resolution fitted to the preference of the user according to the ratio of the exposure times of the imaging elements 151 and 152 and the reflectance of the visible light by the beam splitter BSP1 (refer to FIGS. 5 to 8).

In the 3 mos camera 1A (refer to FIGS. 2 and 4A), the specific wavelength band light is visible light. The beam splitter BSP1 reflects A (A: a predetermined real number) % (for example, 50%) of the visible light that is light transmitted through the dichroic mirror DYM1 and transmits remaining (100−A) % (for example, 50%) of the visible light. A value of A and a value of (100−A) are substantially equal. Accordingly, the 3 mos camera 1A performs the pixel shifting on one of the two video signals having substantially the same brightness (specifically, the first visible video signal V1VD based on the first visible light V1 and the second visible video signal V2VD based on the second visible light V2), then superimposes and combines the signals, and thus can generate the high-resolution video signal WDA having high resolution.

The 3 mos camera 1A performs the pixel shifting on one of the second video signal and the third video signal having substantially the same brightness to generate a fourth video signal (for example, high-resolution video signal WDA) and outputs the video signal (for example, visible/R combined video signal IMVVDA) obtained by combining the fourth video signal and the first video signal (for example, IR video signal N1VD) to the monitor MN1. Accordingly, the 3 mos camera 1A can output, to the monitor MN1, a high-quality video signal obtained by superimposing, for example, the IR video signal N1VD capable of discriminating the details of the fluorescent light emitting part of the diseased part on the high-resolution video signal VVDA having high resolution based on the two video signals having almost the same brightness.

Second Embodiment

In the first embodiment, the 3 mos cameras 1 and 1A have two channels (for example, the imaging elements 151 and 152 shown in FIG. 1 or FIG. 2) for the imaging of the visible light, and superimposes the first visible video signal based on the first visible light and the second visible video signal based on the second visible light, which are respectively imaged by the imaging elements 151 and 152, as appropriate to generate the video signal based on visible light having high sensitivity and wide dynamic range. On the other hand, the IR light has one channel (for example, imaging element 153 shown in FIG. 1 or 2).

In a second embodiment, a 3 mos camera 1B has two channels (for example, imaging elements 151 and 153 shown in FIG. 10) for the imaging of the IR light. The 3 mos camera 1B superimposes a first IR video signal N2VD based on first IR light N2 and a second IR video signal N3VD based on second IR light N3, which are respectively imaged by the imaging elements 151 and 153, as appropriate to generate a video signal capable of discriminating a more detailed state of a diseased part as compared with the first embodiment.

Figure 10:
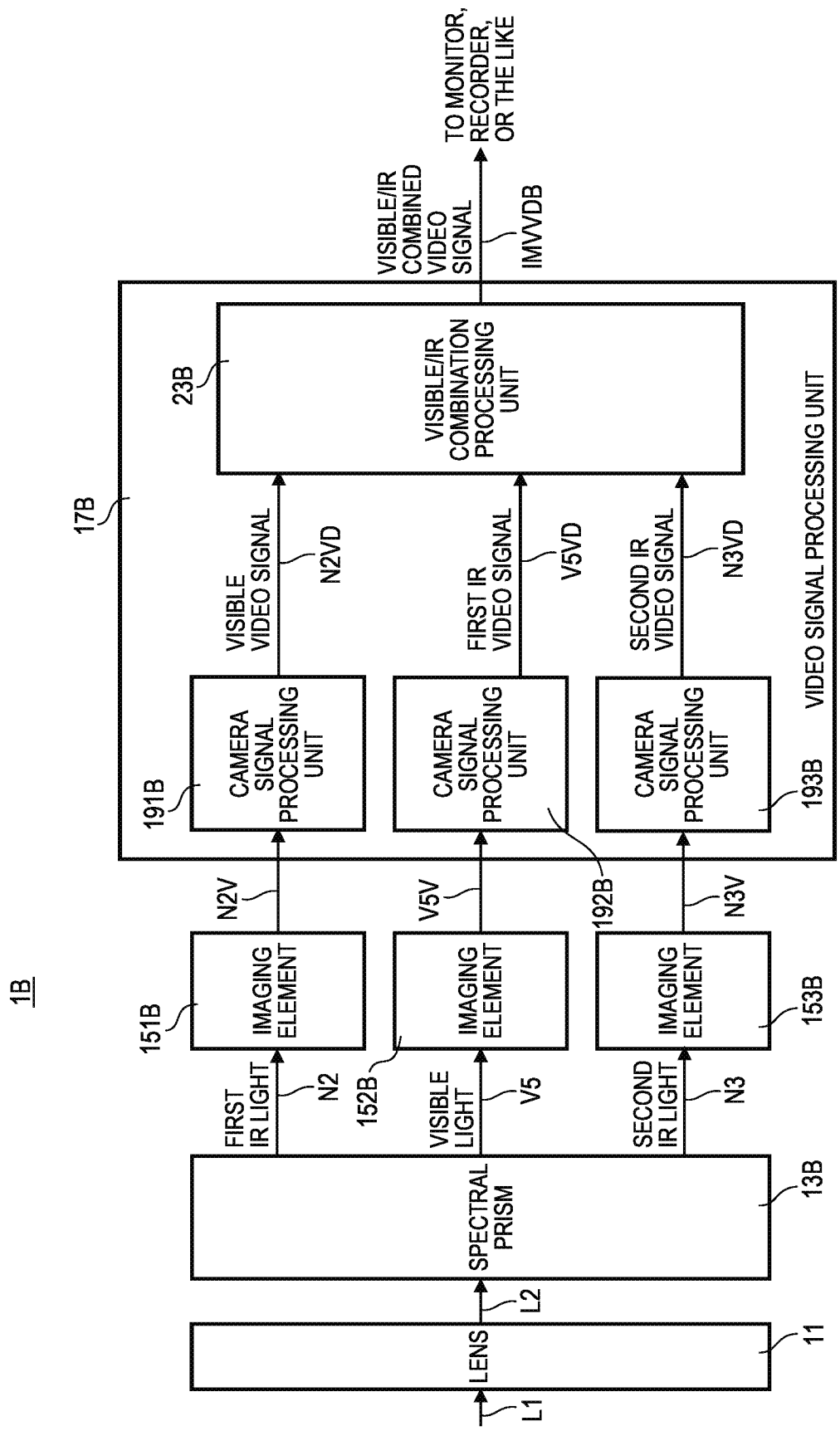
FIG. 10 is a block diagram showing an internal configuration example of a 3 mos camera according to a second embodiment.

FIG. 10 is a block diagram showing an internal configuration example of the 3 mos camera 1B according to the second embodiment. The 3 mos camera 1B is configured to include the lens 11, a spectral prism 13B, imaging elements 151B, 152B, and 153B, and a video signal processing unit 17B. The video signal processing unit 17B has camera signal processing units 191B, 192B, and 193B, and a visible/IR combination processing unit 23B. For each configuration, description of the same configuration as that shown in FIG. 1 or FIG. 2 will be simplified or omitted, and different contents will be described.

The 3 mos camera 1B is used in a medical observation system in which excitation light in a predetermined wavelength band is emitted to a fluorescent reagent (for example, ICG) administered in advance to an observation part (for example, diseased part) in a subject such as a patient at the time of, for example, surgery or examination to image an observation part that emits fluorescent light on long wavelength sides (for example, 700 nm to 800 nm and 800 nm to 900 nm) based on the excitation light. An image (for example, video of the observation part) captured by the 3 mos camera 1B is displayed on the monitor MN1 (refer to FIG. 14) and assists the user such as doctor in executing a medical procedure. The spectral prism 13B will be described as examples used in the medical observation system described above. However, the use thereof is not limited to medical usage and the prism may be used for industrial usage.

The lens 11 is attached to an objective side (tip side) of the spectral prism 13B and collects the light L1 from the observation part (for example, reflected light at the observation part). Collected light L2 is incident on the spectral prism 13B.

The spectral prism 13B receives the light L2 from the observation part and splits the light into the first IR light N2, visible light V5, and the second IR light N3. The spectral prism 13B has a configuration having the IR prism 31, an IR prism 34, and the visible prism 33 (refer to FIG. 11). The first IR light N2 is incident on the imaging element 151 disposed so as to face the IR prism 34. The visible light V5 is incident on the imaging element 152 disposed so as to face the visible prism 33. The second IR light N3 is incident on the imaging element 153 disposed so as to face the IR prism 31. A detailed structural example of the spectral prism 13B will be described below with reference to FIG. 11.

The imaging element 151B as an example of the second image sensor includes, for example, a CCD or a CMOS in which a plurality of pixels suitable for imaging the IR light are arranged. The imaging element 151B is disposed so as to face the IR prism 31 (refer to FIG. 11). The imaging element 151B captures an image based on the incident first IR light N2. The imaging element 151B generates a video signal N2V of the observation part by imaging and outputs the signal to the video signal processing unit 17B.

The imaging element 152B as an example of the third image sensor includes, for example, a CCD or a CMOS in which a plurality of pixels suitable for imaging the visible light are arranged. The imaging element 152B is disposed so as to face the visible prism 33 (refer to FIG. 11). The imaging element 152B captures an image based on the incident visible light V5. The imaging element 152B generates a video signal V5V of the observation part by imaging and outputs the signal to the video signal processing unit 17B.

The imaging element 153B as an example of the first image sensor includes, for example, a CCD or a CMOS in which a plurality of pixels suitable for imaging the IR light are arranged. The imaging element 153B is disposed so as to face the IR prism 31 (refer to FIG. 11). The imaging element 153B captures an image based on the incident second IR light N3. The imaging element 153B generates a video signal N3V of the observation part by imaging and outputs the signal to the video signal processing unit 17B.

The video signal processing unit 17B is configured of a processor such as a DSP or an FPGA. The camera signal processing units 191B to 193B and the visible/IR combination processing unit 23B are executed by the processor described above.

The camera signal processing unit 191B performs various types of camera signal processing using the video signal N2V from the imaging element 151B to generate the first IR video signal N2VD of the observation part, and outputs the signal to the visible/IR combination processing unit 23B. Although details will be described below, the wavelengths of incident light used for imaging are different between the first IR video signal N2VD and the second IR video signal N3VD (refer to FIGS. 12A and 12B).

The camera signal processing unit 192B performs various types of camera signal processing using the video signal V5V from the imaging element 152B to generate a visible video signal VSVD of the observation part, and outputs the signal to the visible/IR combination processing unit 23B.

The camera signal processing unit 193B performs various types of camera signal processing using the video signal N3V from the imaging element 153B to generate the second IR video signal N3VD of the observation part, and outputs the signal to the visible/IR combination processing unit 23B.

The visible/IR combination processing unit 23B inputs and superimposes the first IR video signal N2VD from the camera signal processing unit 191B, the visible video signal VSVD from the camera signal processing unit 192B, and the second IR video signal N3VD from the camera signal processing unit 193B for combining the signals to generated a visible/IR combined video signal IMVVDB. The visible/IR combination processing unit 23B may output the visible/IR combined video signal IMVVDB to the monitor MN1 or send the signal to a recording device (not shown) for accumulation.

Figure 11:
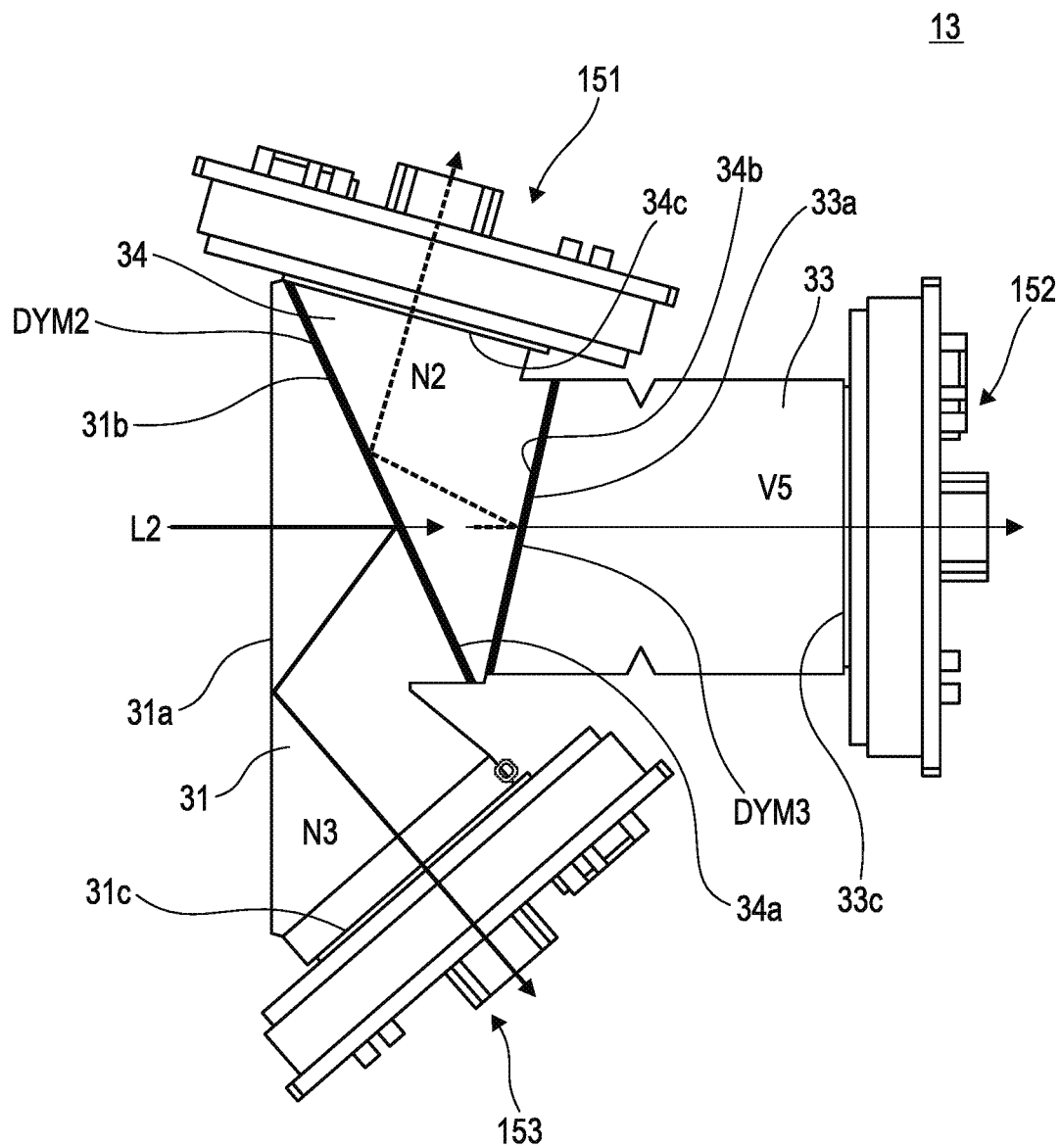
FIG. 11 is a diagram showing a structural example of a spectral prism shown in FIG. 10.

FIG. 11 is a diagram showing a structural example of the spectral prism shown in FIG. 10. The spectral prism 13B has the IR prism 31 (an example of first prism), the IR prism 34 (an example of second prism), and the visible prism 33 (an example of third prism). The IR prism 31, the IR prism 34, and the visible prism 33 are sequentially assembled in an optical axis direction of the light L2 collected by the lens 11.

The IR prism 31 as an example of the first prism includes the incident surface 31a on which the light L2 is incident, the reflection surface 31b on which a dichroic mirror DYM2 that reflects the IR light of the light L2 is formed, and the emission surface 31c from which the IR light is emitted. The dichroic mirror DYM2 (an example of first reflection film) is formed on the reflection surface 31b by vapor deposition or the like, reflects the IR light (for example, IR light in the wavelength band of 800 nm or more) of the light L2, and transmits light of, for example, about 400 nm to 800 nm of the light L2 (refer to FIG. 12A). Specifically, the IR light (for example, IR light in the wavelength band of 800 nm or more) of the light L2 incident on the incident surface 31a of the IR prism 31 is reflected by the reflection surface 31b. This IR light is reflected by the reflection surface 31b, is then totally reflected by the incident surface 31a of the IR prism 31, and is incident on the imaging element 153B through the emission surface 31c.

Figure 12A:
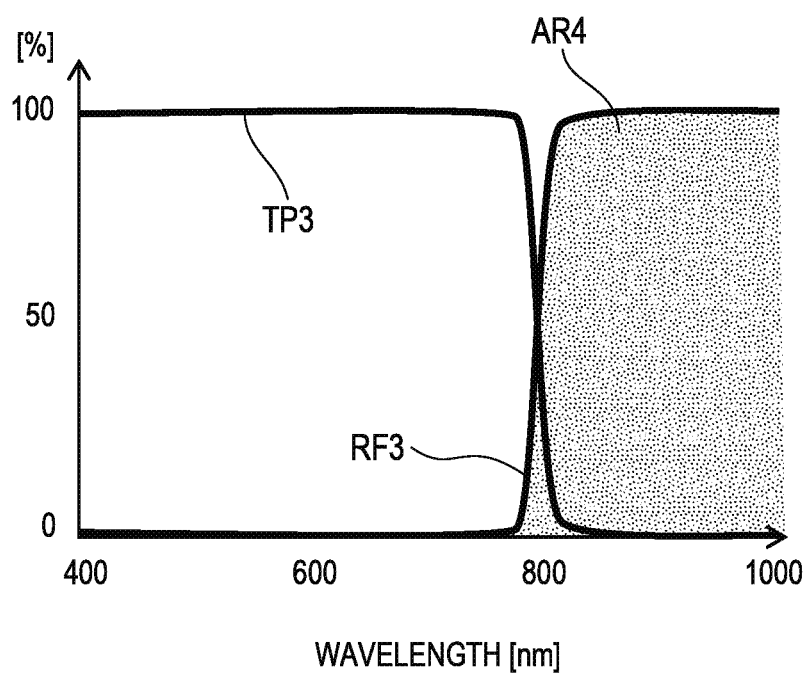
FIG. 12A is a graph showing an example of spectral characteristics of a dichroic mirror.

FIG. 12A is a graph showing an example of spectral characteristics of the dichroic mirror DYM2. The horizontal axis of FIG. 12A indicates wavelength [nm], and the vertical axis indicates reflectance or transmittance. A characteristic TP3 indicates the transmittance of the dichroic mirror DYM2. According to the characteristic TP3, the dichroic mirror DYM2 can transmit the light of about 400 nm to 800 nm. A characteristic RF3 indicates the reflectance of the dichroic mirror DYM2. According to the characteristic RF3, the dichroic mirror DYM2 can reflect the IR light of 800 nm or more. Therefore, all the IR light having a light amount indicated by an area AR4 (in other words, second IR light N3 in the wavelength band of 800 nm or more of the light L2) can be incident on the imaging element 153B.

The IR prism 34 as an example of the second prism includes an incident surface 34a on which the light (an example of first transmitted light) transmitted through the dichroic mirror DYM2 is incident, a reflection surface 34b on which a dichroic mirror DYM3 for reflecting the IR light (first IR light N2) having a 700 nm to 800 nm wavelength band (an example of light in specific wavelength band) of the transmitted light is formed, and an emission surface 34c from which the light (visible light V5) transmitted through the dichroic mirror DYM3 is emitted. The dichroic mirror DYM3 (an example of second reflection film) is formed on the reflection surface 34b by vapor deposition or the like, reflects the IR light in the wavelength band of 700 nm to 800 nm of the light incident on the incident surface 34a, and transmits the visible light V5 in the wavelength band of 400 nm to 700 nm (refer to FIG. 12B). Specifically, the IR light (first IR light N2) in the wavelength band of 700 to 800 nm of the light incident on the incident surface 34a of the IR prism 34 is reflected by the reflection surface 34b. The first IR light N2 is reflected by the reflection surface 34b, is then totally reflected by the incident surface 34a of the IR prism 34, and is incident on the imaging element 151B through the emission surface 34c.

The visible prism 33 as an example of the third prism includes an incident surface 33a on which the visible light V5 (for example, visible light in the wavelength band of 400 to 700 nm) transmitted through the dichroic mirror DYM3 is incident and an emission surface 33c from which the visible light V5 is emitted. Specifically, the visible light V5 transmitted through the dichroic mirror DYM3 is incident on the visible prism 33, is emitted as it is, and is incident on the imaging element 152B (refer to FIG. 12C).

Figure 12B:
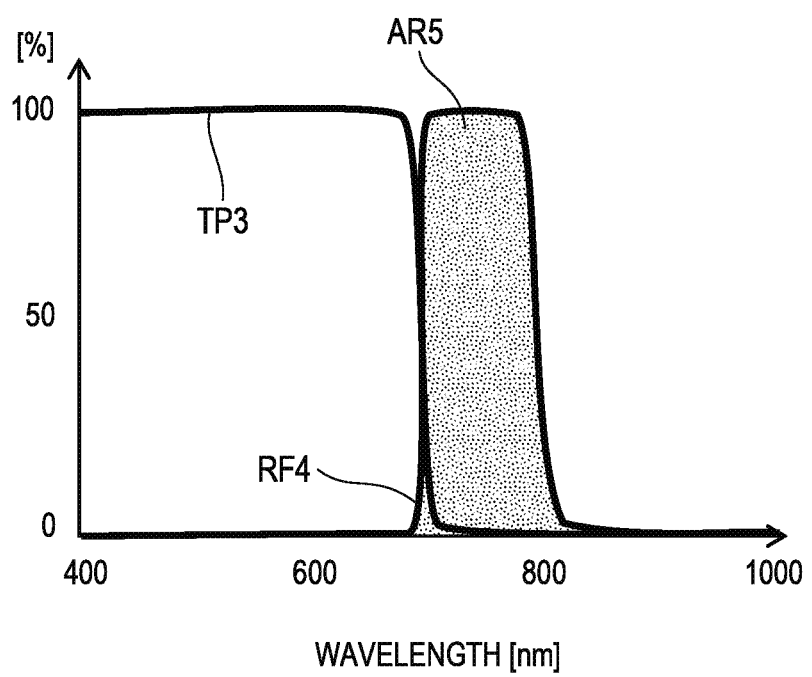
FIG. 12B is a graph showing an example of spectral characteristics of the dichroic mirror.
Figure 12C:
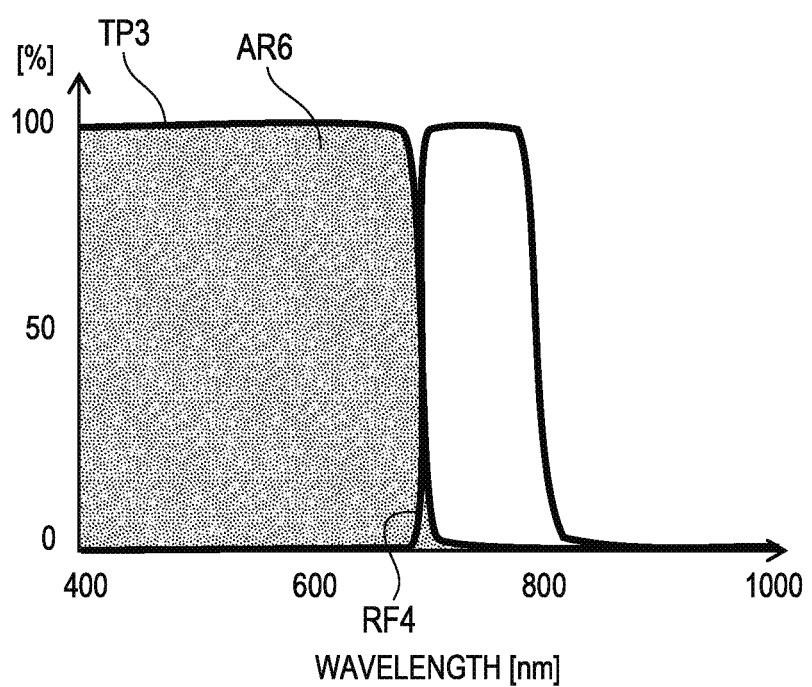
FIG. 12C is a graph showing an example of spectral characteristics of the dichroic mirror.

FIGS. 12B and 12C are graphs showing examples of spectral characteristics of the dichroic mirror DYM3. In FIGS. 12B and 12C, the horizontal axis indicates wavelength [nm] and the vertical axis indicates reflectance or transmittance. The characteristic TP3 indicates the transmittance (400 nm to 700 nm is transmittable) of the dichroic mirror DYM3 in the spectral prism 13B shown in FIG. 11, and a characteristic RF4 indicates the reflectance (700 nm to 800 nm is reflectable) of the dichroic mirror DYM3 in the spectral prism 13B shown in FIG. 11. According to the characteristic TP3 and the characteristic RF4, the dichroic mirror DYM3 as an example of the second reflection film can reflect the IR light of about 700 nm to 800 nm and transmit the visible light of 400 nm to 700 nm. Therefore, IR light having a light amount indicated by an area AR5 can be incident on the imaging element 151.

As shown in FIG. 12C, the dichroic mirror DYM3 can reflect the IR light of about 700 nm to 800 nm and transmit the visible light of 400 nm to 700 nm. Visible light having a light amount indicated by an area AR6 can be incident on the imaging element 152.

Figure 13:
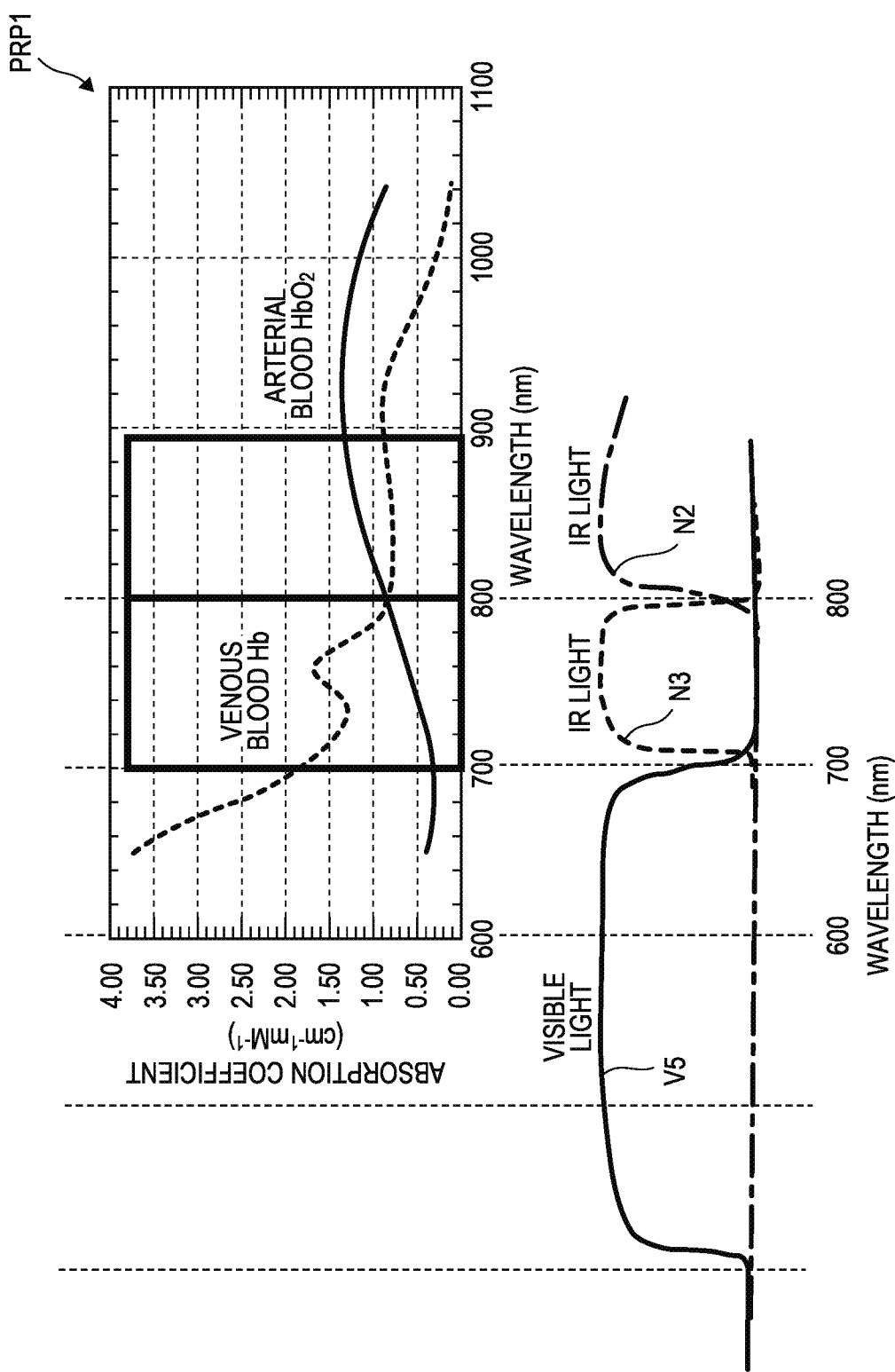
FIG. 13 is a graph showing an example of a relationship between visible light, first IR light, and second IR light.

FIG. 13 is a graph showing an example of a relationship between the visible light V5, the first IR light N2, and the second IR light N3. In the second embodiment, the spectral prism 13B splits the light L2 into IR light in two wavelength bands (specifically, first IR light N2 having wavelength of 800 nm or more and second IR light N3 having wavelength of 700 nm to 800 nm). In a characteristic diagram PRP1 of FIG. 13, the horizontal axis indicates wavelength [nm], and the vertical axis indicates transition of each absorption coefficient of arterial blood and venous blood for each wavelength. According to the characteristic diagram PRP1 of FIG. 13, the absorption coefficient of venous blood is higher than that of arterial blood in the wavelength band of 700 nm to 800 nm, and conversely, the absorption coefficient of arterial blood is higher than that of venous blood in the wavelength band of 800 nm to 900 nm. Therefore, it is possible to identify between arterial blood and venous blood by a ratio of the second IR light N3 and the first IR light N2. As described above, it is possible to capture an image with the visible light V5 in the wavelength band of 400 nm to 700 nm.

Figure 14:
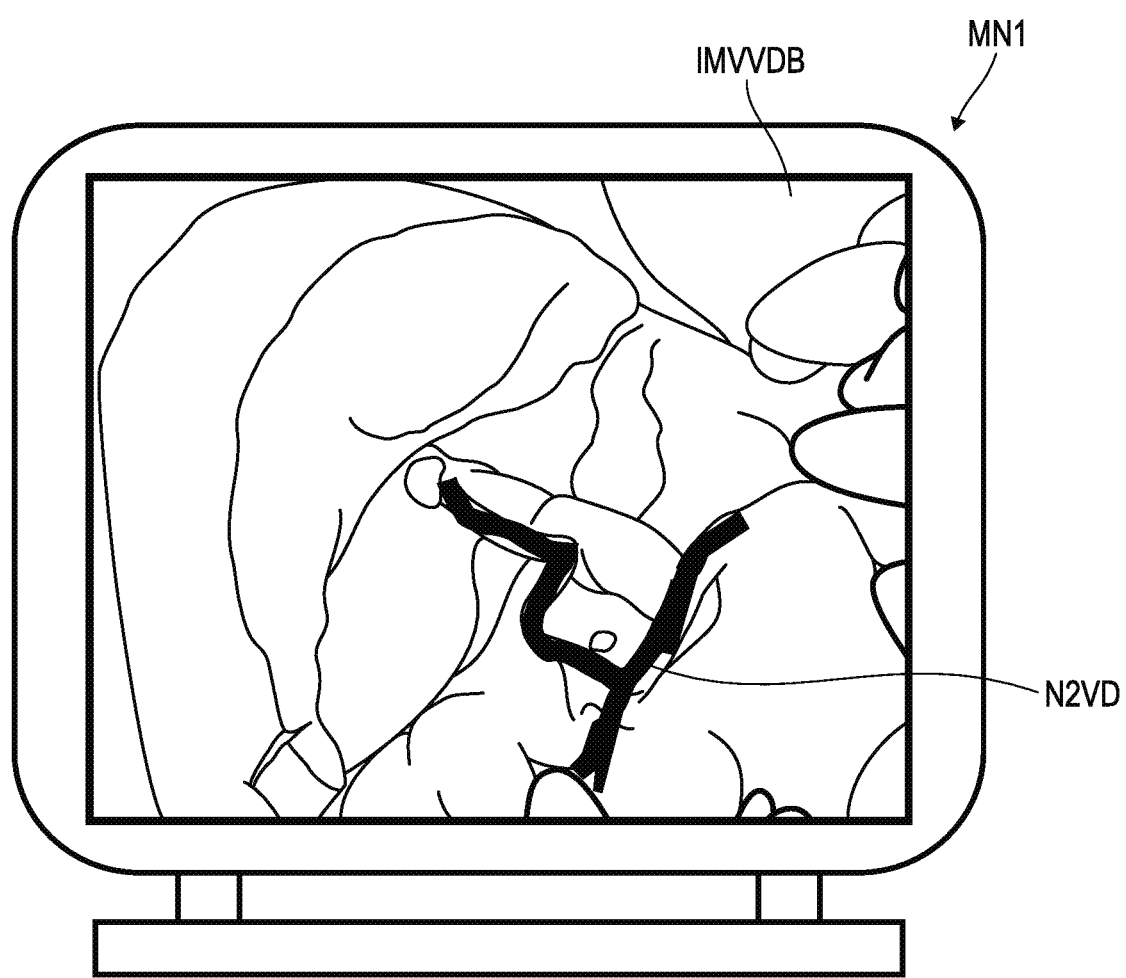
FIG. 14 is a diagram showing a display example of a visible/IR combined video signal generated by the 3 mos camera according to the second embodiment on a monitor.

FIG. 14 is a diagram showing a display example of the visible/IR combined video signal IMVVDB generated by the 3 mos camera 1B according to the second embodiment on the monitor MN1. The visible/IR combined video signal IMVVDB shown in FIG. 14 is generated based on imaging at the observation part (for example, around liver and pancreas) of the patient who is the subject and is displayed on the monitor MN1. Particularly in the second embodiment, the visible/IR combined video signal IMVVDB can allow the user such as doctor to grasp in detail whether a vein or an artery is present at the observation part, with the combination of the first IR video signal N2VD and the second IR video signal N3VD based on the imaging of the first IR light N2 and the second IR light N3 separated (split) into two types of wavelength bands. In FIG. 14, the presence of the artery is indicated by the first IR video signal N2VD. In this manner, the 3 mos camera 1B generates a high-quality visible/R combined video signal IMVVDB that allows the user such as doctor to grasp the details of the observation part (in particular, presence or absence of vein and artery) at the time of, for example, surgery or examination, and displays the signal on the monitor MN1.

In the 3 mos camera 1B (refer to FIGS. 10, 12A, and 12B), the specific wavelength band light is IR light. The dichroic mirror DYM2 reflects IR light having a specific wavelength (for example, 800 nm) or more among IR components of the light L2 incident on the spectral prism 1B. The dichroic mirror DYM3 reflects IR light having a wavelength less than a specific wavelength (for example, 700 nm to 800 nm) among IR components of the light transmitted through the dichroic mirror DYM2. Accordingly, the 3 mos camera 1B can allow the user such as doctor to grasp in detail whether a vein or an artery is present at the observation part of the subject, with the combination of the first IR video signal N2VD and the second IR video signal N3VD based on the imaging of the first IR light N2 and the second IR light N3 separated (split) into two types of wavelength bands.

Although various embodiments are described with reference to the drawings, it goes without saying that the present disclosure is not limited to such examples. It is obvious to those skilled in the art that various modification examples, change examples, substitution examples, addition examples, deletion examples, and equivalent examples can be conceived within the scope of the claims. Of course, it is understood that the various examples belong to the technical scope of the present disclosure. Further, the respective constituent elements in the various embodiments described above may be randomly combined in the scope of not departing from the spirit of the invention.

The present disclosure is useful as the 3 mos camera that generates and outputs the clearer fluorescence image of the observation part to which the fluorescent reagent is administered and assists the doctor or the like in easily grasping the diseased part.

The present application is based upon Japanese Patent Application (Patent Application No. 2019-199182 filed on Oct. 31, 2019), the content of which is incorporated herein by reference.

What is claimed is:

1. A 3 MOS camera used during a medical procedure, the 3 MOS camera comprising:
   a first prism that:
      has a first reflection film which reflects IR light of light from an observation part; and
      causes a first image sensor to receive the IR light;
   a second prism that:
      has a second reflection film which reflects A % (A: a predetermined real number) visible light transmitted through the first reflection film and which transmits remaining (100−A) % visible light; and
      causes a second image sensor to receive the A % visible light;
   a third prism that causes a third image sensor to receive the (100−A) % visible light transmitted through the second reflection film; and
   a video signal processor that:
      generates a first video signal, a second video signal, and a third video signal of the observation part based on respective imaging outputs of the first image sensor, the second image sensor, and the third image sensor;
      combines the first video signal, the second video signal, and the third video signal to generate a first combined video signal;
      outputs the first combined video signal to a monitor;
      performs pixel shifting on one of the second video signal and the third video signal both having substantially same brightness as each other to generate a fourth video signal; and outputs a second combined video signal, obtained by combining the fourth video signal and the first video signal, to the monitor.

2. The 3 MOS camera according to claim 1, wherein the video signal processor:
   combines the second video signal and the third video signal both having different brightness from one another to generate a fifth video signal; and
   outputs a third combined video signal, obtained by combining the fifth video signal and the first video signal, to the monitor.

3. The 3 MOS camera according to claim 1, wherein the video signal processor controls a ratio of exposure times of the second image sensor and the third image sensor to be same as each other.

4. The 3 MOS camera according to claim 1, wherein the video signal processor controls a ratio of exposure times of the second image sensor and the third image sensor to be different from one another.

5. A 3 MOS camera configured to be used during a medical procedure, the 3 MOS camera comprising:
   a first prism that:
      includes a first reflection film which reflects IR light of light from an observation part; and
      causes a first image sensor to receive the IR light;
   a second prism that:
      includes a second reflection film which reflects a first percent of visible light transmitted through the first reflection film and which transmits a second percent of the visible light; and
      causes a second image sensor to receive the first percent of the visible light;
   a third prism that causes a third image sensor to receive the second percent of the visible light transmitted through the second reflection film; and
   a processor that:
      generates a first video signal, a second video signal, and a third video signal of the observation part based on respective imaging outputs of the first image sensor, the second image sensor, and the third image sensor;
      combines the first video signal, the second video signal, and the third video signal to generate a first combined video signal;
      performs pixel shifting on one of the second video signal and the third video signal, with both having a substantially same brightness, to generate a fourth video signal;
      combines the fourth video signal and the first video signal to generate a second combined video signal; and
      outputs the first combined video signal and the second combined video signal to a monitor,
   wherein the first percent is a real number divided by one hundred, and
   the first percent plus the second percent equals one hundred percent.

6. The 3 MOS camera according to claim 1, wherein the processor:
   combines the second video signal and the third video signal, with each having a different brightness, to generate a fifth video signal;
   combines the fifth video signal and the first video signal to generate a third combined video signal; and
   outputs the third combined video signal to the monitor.

7. The 3 MOS camera according to claim 1, wherein the processor controls a ratio of exposure times of the second image sensor and the third image sensor to be same.

8. The 3 MOS camera according to claim 1, wherein the processor controls a ratio of exposure times of the second image sensor and the third image sensor to be different.

* * * * *